United States Patent
Gruenbacher et al.

(10) Patent No.: US 10,076,585 B2
(45) Date of Patent: Sep. 18, 2018

(54) METHOD OF DELIVERING A DOSE OF A FLUID COMPOSITION FROM A MICROFLUIDIC DELIVERY CARTRIDGE

(71) Applicant: The Procter & Gamble Company, Cincinnati, OH (US)

(72) Inventors: Dana Paul Gruenbacher, Fairfield, OH (US); Stephan Gary Bush, Liberty Township, OH (US); Teck Khim Neo, Singapore (SG); David S. Hunt, San Diego, CA (US); Joseph Edward Scheffelin, Poway, CA (US); Steven L Webb, Murrieta, CA (US); Domenico Giusti, Cornaredo (IT); Simon Dodd, West Linn, OR (US); Faiz Feisal Sherman, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 293 days.

(21) Appl. No.: 14/310,367

(22) Filed: Jun. 20, 2014

(65) Prior Publication Data
US 2015/0367014 A1 Dec. 24, 2015

(51) Int. Cl.
*A61L 9/03* (2006.01)
*A45D 34/00* (2006.01)
(Continued)

(52) U.S. Cl.
CPC .............. *A61L 9/03* (2013.01); *A45D 34/00* (2013.01); *A61L 9/037* (2013.01); *B41J 2/0458* (2013.01); *B41J 2/04581* (2013.01); *B41J 2/04588* (2013.01); *B41J 2/14024* (2013.01); *B41J 2/14072* (2013.01); *B41J 2/14145* (2013.01); *A61L 2209/133* (2013.01); *A61L 2209/134* (2013.01)

(58) Field of Classification Search
CPC ................ A61L 9/03; A61L 2209/134; A61L 2209/133; B41J 2/0458; B41J 2/04581; B41J 2/14024; B41J 2/14145; B41J 2/14072
USPC ....... 219/201; 347/7, 18, 29, 62, 85, 86, 87; 424/43, 76.1, 76.3, 405
See application file for complete search history.

(56) References Cited

U.S. PATENT DOCUMENTS 3,465,350 A  9/1969 Keur et al.
3,465,351 A  9/1969 Keur et al.
(Continued)

FOREIGN PATENT DOCUMENTS

CA  2 213 066 A1  2/1999
CN  1223637 C  10/2005
(Continued)

OTHER PUBLICATIONS

U.S. Appl. No. 14/310,401, filed Jun. 20, 2014, Dana Paul Gruenbacher, et al.
(Continued)

*Primary Examiner* — Thien S Tran
(74) *Attorney, Agent, or Firm* — Abbey A. Lopez

(57) ABSTRACT

Microfluidic delivery systems and methods for dispensing a fluid composition into the air comprising microfluidic die and at least one heating element that is configured to receive an electrical signal comprising a certain on-time and wave form to deliver a fluid composition into the air.

8 Claims, 14 Drawing Sheets

(51) Int. Cl.
*B41J 2/045* (2006.01)
*B41J 2/14* (2006.01)

(56) References Cited

U.S. PATENT DOCUMENTS

| | | | |
|---|---|---|---|
| 3,967,286 A | 6/1976 | Andersson et al. | |
| 4,463,359 A * | 7/1984 | Ayata | B41J 2/04533 346/3 |
| 4,532,530 A * | 7/1985 | Hawkins | B41J 2/14129 347/62 |
| 5,084,713 A | 1/1992 | Wong | |
| 5,317,339 A | 5/1994 | Braun | |
| 5,591,409 A | 1/1997 | Watkins | |
| 5,610,635 A | 3/1997 | Murray | |
| 5,666,140 A | 9/1997 | Mitani et al. | |
| 5,714,989 A | 2/1998 | Wade et al. | |
| 5,874,974 A | 2/1999 | Courian et al. | |
| 5,975,675 A | 11/1999 | Kim | |
| 6,010,210 A | 1/2000 | Wilson et al. | |
| 6,012,799 A * | 1/2000 | Silverbrook | B41J 2/14451 347/43 |
| 6,024,440 A | 2/2000 | Murthy et al. | |
| 6,113,228 A | 9/2000 | Pawlowski | |
| 6,126,277 A | 10/2000 | Feinn et al. | |
| 6,139,131 A | 10/2000 | Prasad et al. | |
| 6,170,937 B1 | 1/2001 | Childers et al. | |
| 6,261,347 B1 | 7/2001 | Moreland | |
| 6,282,458 B1 | 8/2001 | Muray et al. | |
| 6,287,550 B1 | 9/2001 | Trinh | |
| 6,322,200 B1 | 11/2001 | Feinn et al. | |
| 6,325,475 B1 | 12/2001 | Hayes et al. | |
| 6,371,451 B1 | 4/2002 | Chol | |
| 6,543,887 B2 | 4/2003 | Chang | |
| 6,672,129 B1 | 1/2004 | Frederickson et al. | |
| 6,698,862 B1 * | 3/2004 | Choi | B41J 2/04528 347/17 |
| 6,808,684 B2 | 10/2004 | Boden et al. | |
| 6,834,937 B2 | 12/2004 | Killmeier | |
| 7,097,263 B2 | 8/2006 | Silverbrook | |
| 7,201,916 B2 | 4/2007 | Schiavo | |
| 7,223,361 B2 | 5/2007 | Kvietok et al. | |
| 7,293,849 B2 | 11/2007 | Tani et al. | |
| 7,328,974 B2 | 2/2008 | Wang | |
| 7,367,661 B2 | 5/2008 | Hess et al. | |
| 7,389,943 B2 | 6/2008 | Jaworski | |
| 7,490,815 B2 | 2/2009 | Tollens et al. | |
| 7,499,632 B2 | 3/2009 | Granger | |
| 8,020,573 B2 | 9/2011 | Lamers et al. | |
| 8,087,759 B2 | 1/2012 | Oikawa et al. | |
| 8,101,124 B2 | 1/2012 | Uchiyama | |
| 8,142,558 B2 | 3/2012 | Robertson et al. | |
| 8,201,752 B2 | 6/2012 | Brodbeck | |
| 8,251,500 B2 | 8/2012 | Yamanda et al. | |
| 8,727,234 B2 | 5/2014 | Haran | |
| 8,821,802 B2 | 9/2014 | Haran | |
| 8,870,090 B2 | 10/2014 | Feriani | |
| 8,881,999 B2 | 11/2014 | Blaylock et al. | |
| 9,174,453 B1 | 11/2015 | Dodd et al. | |
| 9,211,356 B2 | 12/2015 | Gruenbacher et al. | |
| 9,211,980 B1 | 12/2015 | Gruenbacher | |
| 9,377,786 B2 | 6/2016 | Nakamoto et al. | |
| 9,554,459 B2 | 1/2017 | Gruenbacher et al. | |
| 9,636,430 B2 | 5/2017 | Gruenbacher et al. | |
| 2001/0050317 A1 | 12/2001 | Denen | |
| 2002/0050533 A1 | 5/2002 | Hirota | |
| 2002/0063752 A1 | 5/2002 | Clark | |
| 2002/0086319 A1 | 7/2002 | Elison et al. | |
| 2002/0192255 A1 * | 12/2002 | Schiavo | A01M 1/2077 424/405 |
| 2003/0062385 A1 | 4/2003 | Engel | |
| 2003/0218077 A1 | 11/2003 | Boticki | |
| 2004/0032468 A1 | 2/2004 | Killmeier et al. | |
| 2004/0119793 A1 | 6/2004 | Mutz et al. | |
| 2004/0200907 A1 | 10/2004 | Martens et al. | |
| 2005/0018016 A1 * | 1/2005 | Silverbrook | B41J 2/14314 347/54 |
| 2005/0037945 A1 | 2/2005 | Gygax et al. | |
| 2005/0062804 A1 | 3/2005 | Eaton | |
| 2005/0077376 A1 | 4/2005 | Hess et al. | |
| 2005/0091879 A1 | 5/2005 | DuVal et al. | |
| 2005/0124512 A1 | 6/2005 | Woo et al. | |
| 2005/0205916 A1 | 9/2005 | Conway et al. | |
| 2005/0279854 A1 | 12/2005 | Martens et al. | |
| 2006/0065755 A1 | 3/2006 | Sugita et al. | |
| 2006/0152550 A1 | 7/2006 | Tomita | |
| 2007/0008380 A1 | 1/2007 | Ushinohama | |
| 2007/0010645 A1 | 1/2007 | Vonwiller et al. | |
| 2007/0207174 A1 | 9/2007 | Pluyter | |
| 2008/0023569 A1 | 1/2008 | O'Leary et al. | |
| 2008/0043063 A1 | 2/2008 | Bergstedt | |
| 2008/0061163 A1 | 3/2008 | Kubby et al. | |
| 2008/0073443 A1 | 3/2008 | Tollens | |
| 2008/0197213 A1 | 8/2008 | Flashinski et al. | |
| 2009/0096839 A1 | 4/2009 | Olbrich et al. | |
| 2009/0108094 A1 | 4/2009 | Irvi | |
| 2009/0126722 A1 | 5/2009 | Sugita et al. | |
| 2009/0289127 A1 | 11/2009 | Tollens | |
| 2010/0001091 A1 | 1/2010 | Bara et al. | |
| 2010/0154790 A1 | 6/2010 | Merassi et al. | |
| 2010/0206306 A1 | 8/2010 | Feriani et al. | |
| 2010/0328957 A1 | 12/2010 | Hessing | |
| 2011/0024521 A1 | 2/2011 | Joergensen | |
| 2011/0036365 A1 | 2/2011 | Chong et al. | |
| 2011/0049266 A1 | 3/2011 | Joergensen | |
| 2011/0089252 A1 | 4/2011 | Rosener et al. | |
| 2011/0130877 A1 | 6/2011 | Lynch | |
| 2011/0221083 A1 | 9/2011 | Laulicht | |
| 2011/0284653 A1 | 11/2011 | Butler et al. | |
| 2011/0284656 A1 | 11/2011 | Kambayashi et al. | |
| 2011/0290911 A1 | 12/2011 | Tollens et al. | |
| 2012/0093491 A1 | 4/2012 | Browder et al. | |
| 2012/0097754 A1 * | 4/2012 | Vlad | A61L 9/01 239/6 |
| 2013/0010035 A1 | 1/2013 | Norikane | |
| 2013/0026250 A1 | 1/2013 | Burt | |
| 2013/0206857 A1 | 8/2013 | Ivri | |
| 2013/0292484 A1 | 11/2013 | Jackson | |
| 2014/0369895 A1 | 12/2014 | Turner et al. | |
| 2015/0367013 A1 | 12/2015 | Gruenbacher et al. | |
| 2015/0367014 A1 | 12/2015 | Gruenbacher et al. | |
| 2015/0367016 A1 | 12/2015 | Gruenbacher et al. | |
| 2015/0367356 A1 | 12/2015 | Gruenbacher et al. | |
| 2015/0368001 A1 | 12/2015 | Gruenbacher et al. | |
| 2016/0271639 A1 | 9/2016 | Bush et al. | |
| 2016/0354799 A1 | 12/2016 | Gruenbacher et al. | |
| 2017/0072085 A1 | 3/2017 | Gruenbacher et al. | |
| 2017/0072086 A1 | 3/2017 | Gruenbacher et al. | |
| 2017/0094720 A1 | 3/2017 | Gruenbacher et al. | |
| 2017/0165390 A1 | 6/2017 | Gruenbacher et al. | |

FOREIGN PATENT DOCUMENTS

| | | |
|---|---|---|
| CN | 204072869 U | 1/2015 |
| EP | 1510228 A1 | 3/2005 |
| EP | 1894727 A2 | 3/2008 |
| EP | 2143576 B1 | 11/2012 |
| JP | H09123453 A | 5/1997 |
| JP | 2002254613 A | 9/2002 |
| JP | A-2004-311093 | 11/2004 |
| JP | 2005185366 A | 7/2005 |
| JP | A-2008-168223 | 7/2005 |
| JP | 2005224503 A | 8/2005 |
| JP | 2005224504 A | 8/2005 |
| JP | A2005224504 | 8/2005 |
| JP | 2007054446 A | 3/2007 |
| JP | A-2008-061937 | 3/2008 |
| JP | A-2009-213901 | 9/2009 |
| KR | 100238582 B1 | 1/2000 |
| WO | WO 01/30404 A1 | 5/2001 |
| WO | WO 2004/044552 A2 | 5/2004 |
| WO | WO 2006/004902 A1 | 1/2006 |

(56) References Cited

FOREIGN PATENT DOCUMENTS

| WO | WO 2007/083164 A2 | 7/2007 |
|---|---|---|
| WO | WO 2014/043424 A1 | 3/2014 |
| WO | WO 2015/175527 A2 | 11/2015 |

OTHER PUBLICATIONS

U.S. Appl. No. 14/310,285, filed Jun. 20, 2014, Dana Paul Gruenbacher, et al.
U.S. Appl. No. 14/310,311, filed Jun. 20, 2014, Dana Paul Gruenbacher, et al.
U.S. Appl. No. 14/310,334, filed Jun. 20, 2014, Dana Paul Gruenbacher, et al.
PCT Search Report dated Jun. 19, 2015; PCT/US2015/036546, 5 Pages.
PCT Search Report dated Sep. 17, 2015; PCT/US2015/036549, 11 Pages.
PCT Search Report dated Sep. 18, 2015; PCT/US2015/036551, 9 pages.
All Office Actions for U.S. Appl. No. 14/310,401.
All Office Actions for U.S. Appl. No. 14/310,285.
All Office Actions for U.S. Appl. No. 14/950,214.
All Office Actions for U.S. Appl. No. 14/310,311.
All Office Actions for U.S. Appl. No. 14/310,334.
All Office Actions for U.S. Appl. No. 14/024,673.
All Office Actions for U.S. Appl. No. 14/217,524.
All Office Actions for U.S. Appl. No. 14/658,280.
All Office Actions for U.S. Appl. No. 15/231,807.
All Office Actions for U.S. Appl. No. 15/376,691.
All Office Actions for U.S. Appl. No. 14/966,231.
All Office Actions for U.S. Appl. No. 15/358,171.
All Office Actions for U.S. Appl. No. 14/855,653.
All Office Actions for U.S. Appl. No. 14/855,662.
All Office Actions for U.S. Appl. No. 14/855,677.

* cited by examiner

METHOD OF DELIVERING A DOSE OF A FLUID COMPOSITION FROM A MICROFLUIDIC DELIVERY CARTRIDGE

FIELD OF THE INVENTION

The present invention relates to a microfluidic delivery system comprising a microfluidic delivery member and methods for delivering a fluid composition into the air.

BACKGROUND OF THE INVENTION

Various systems exist to deliver fluid compositions, such as perfume mixtures, into the air by an energized (i.e. electrically/battery powered) atomization system. Such systems include battery-powered automatic aerosol air fresheners, sold under the tradename AirWick® by Reckitt Benckiser. Another attempt is a piezoelectric actuator that atomizes a volatile composition into fluid droplets in the air, sold under the tradename Glade® by S.C. Johnson & Son.

Recent attempts have been made to deliver fluid compositions, including scented inks, by means of an ink jet spray head. These attempts are directed to emitting a fluid composition onto an adjacent substrate/surface or emitting a fluid composition into an adjacent space. For example, JP2007054445A1 describes an ink jet head that sprays fluids into a personal space (e.g. near a user's nose) for attaining a benefit. JP2005125225 describes an ink jet head that sprays an insecticide towards a target surface.

There remains a need for an improved microfluidic delivery system to efficiently deliver sufficient quantities of a fluid composition into the air to deliver a benefit, e.g., freshen a room or living space, with minimal deposition of the fluid composition onto adjacent surfaces.

SUMMARY OF THE INVENTION

In one embodiment, there is provided a method of delivering a dose of a liquid composition from a microfluidic delivery refill, wherein the liquid composition comprises volatile components such that the liquid composition is defined by a flash point temperature and a boiling point temperature, and wherein the microfluidic delivery refill comprises a reservoir enclosing the liquid composition and a microfluidic delivery member comprising a heater in fluid communication with the reservoir, the method comprising:
deactivating the heater of the microfluidic delivery member, wherein, when the heater is deactivated, a temperature of the heater is less than the flash point temperature of the liquid composition;
receiving an electrical signal with the heater of the microfluidic delivery member; activating the heater of the microfluidic delivery member in response to the electrical signal, wherein, when the heater is activated, the temperature of the heater is greater than the boiling point temperature of the liquid composition; and
vaporizing at least a portion of the volatile components of the liquid composition when the heater is activated, whereby the dose of the liquid composition is delivered from the microfluidic delivery member.

DETAILED DESCRIPTION OF THE DRAWINGS

Figure 1:
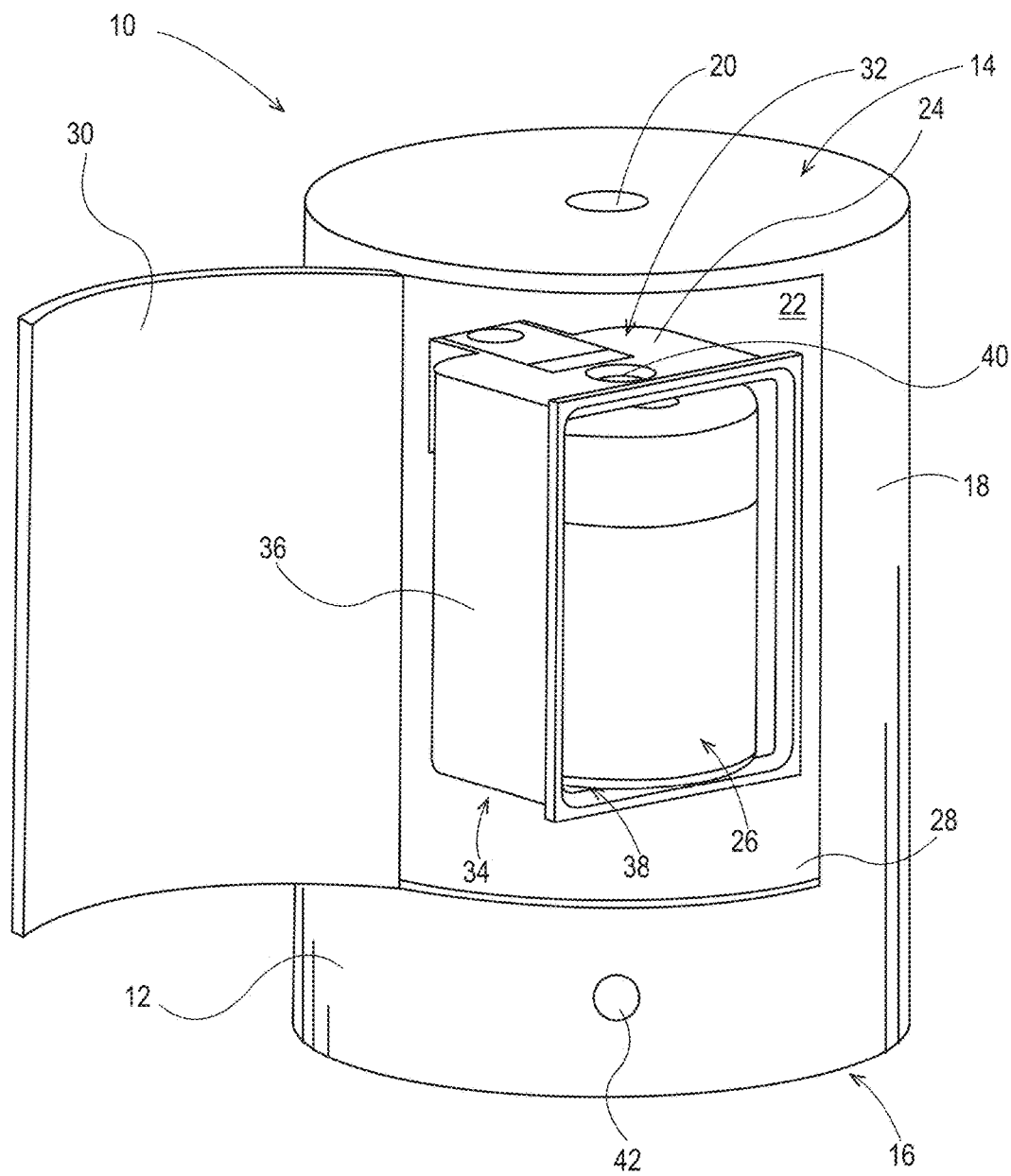
FIG. 1 is a schematic isometric view of a microfluidic delivery system in accordance with one embodiment.
Figure 2A:
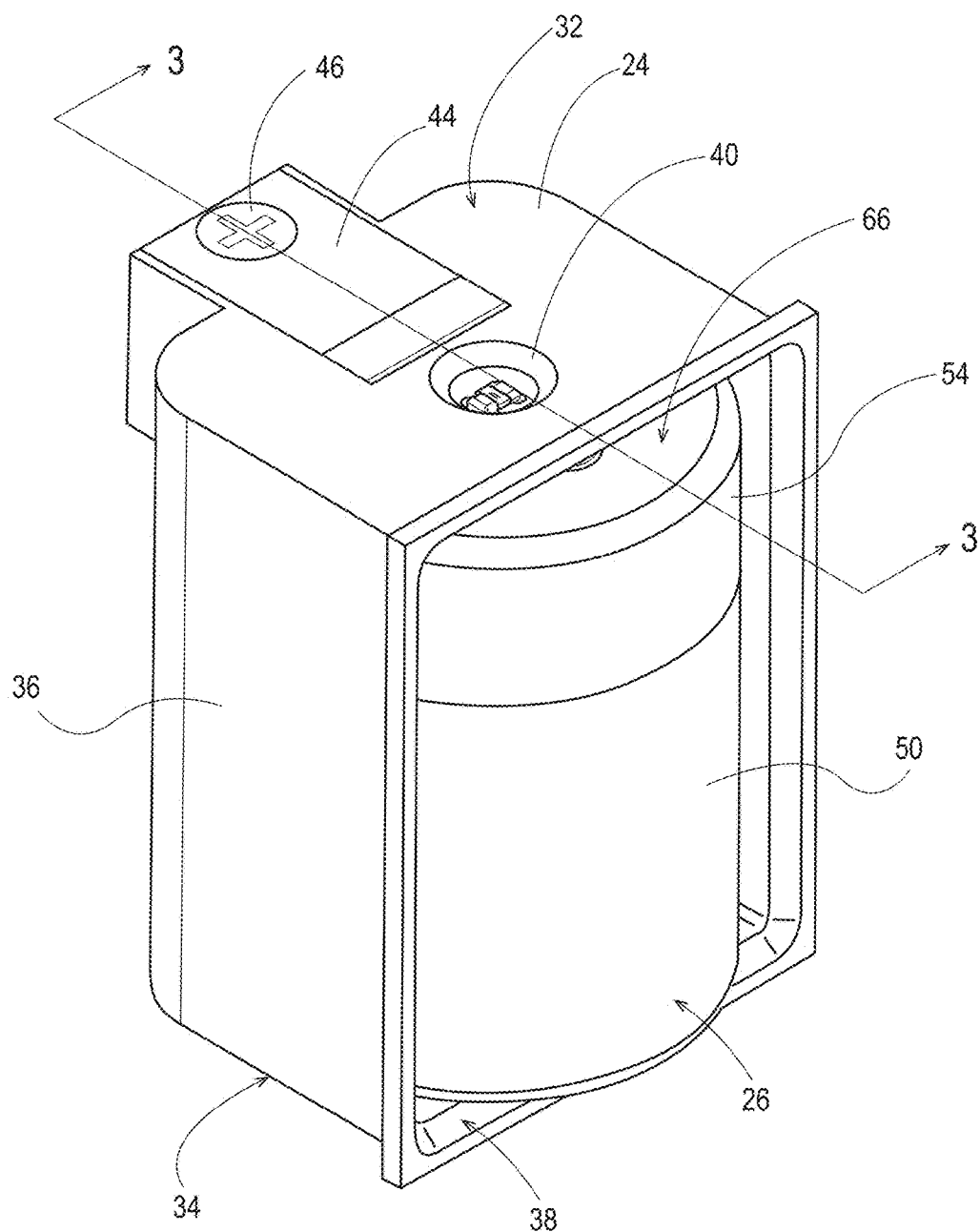
FIG. 2A is a schematic isometric view of a microfluidic delivery cartridge and a holder in accordance with one embodiment.
Figure 3:
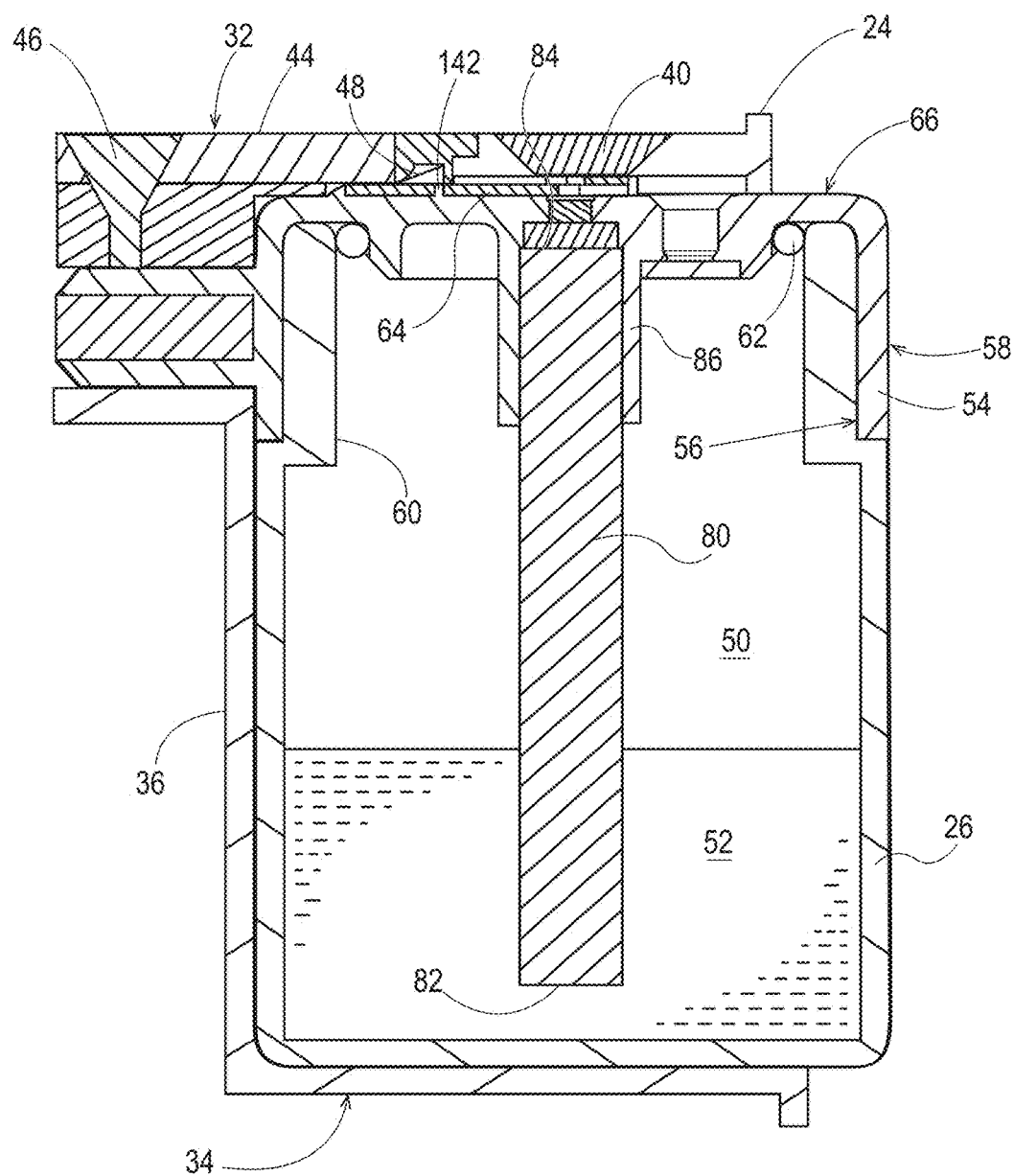

FIG. 3. is a cross-section schematic view of line 3-3 in FIG. 2A.

Figure 2B:
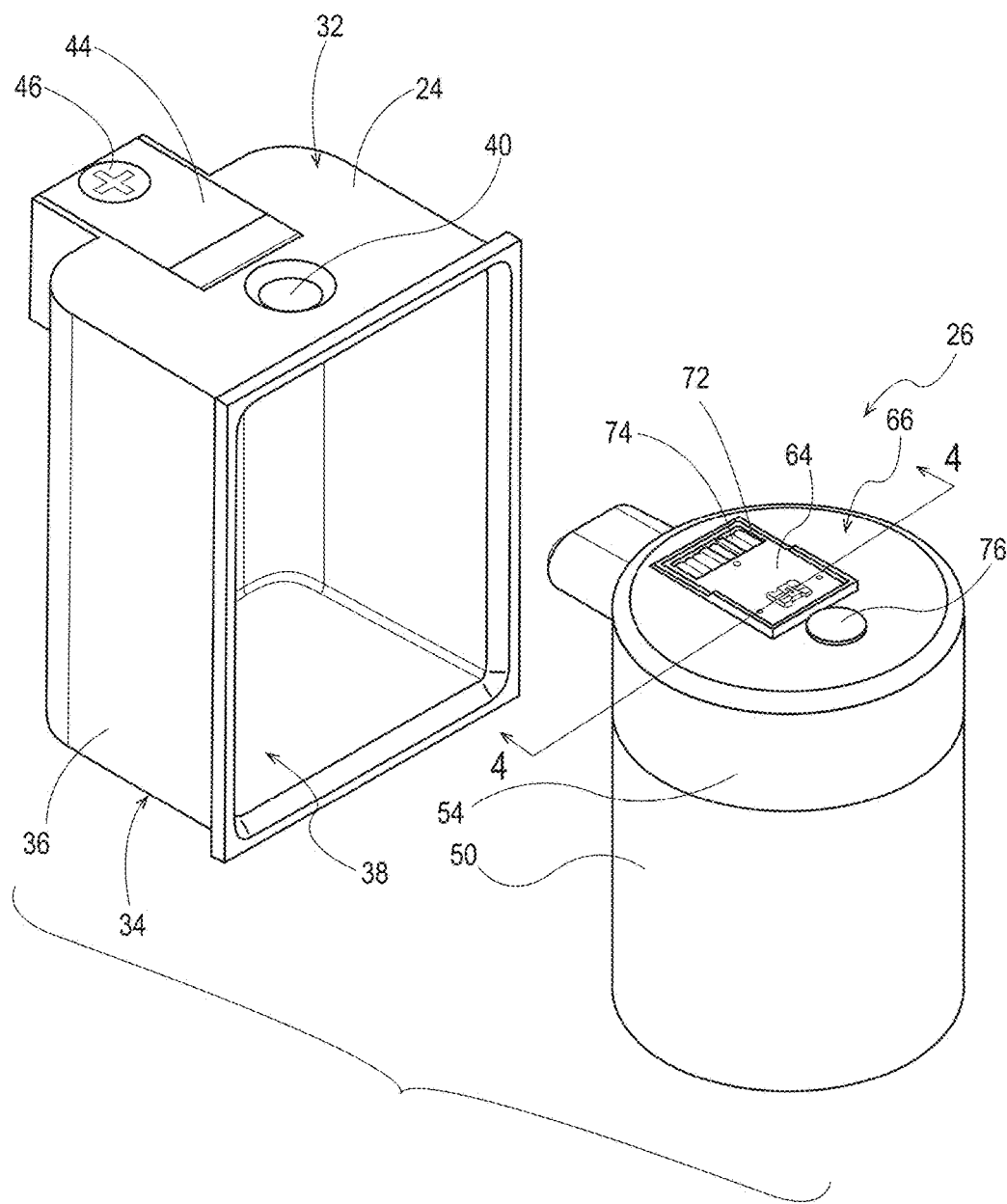
FIG. 2B is an exploded view of the structure in FIG. 2A.
Figure 4:
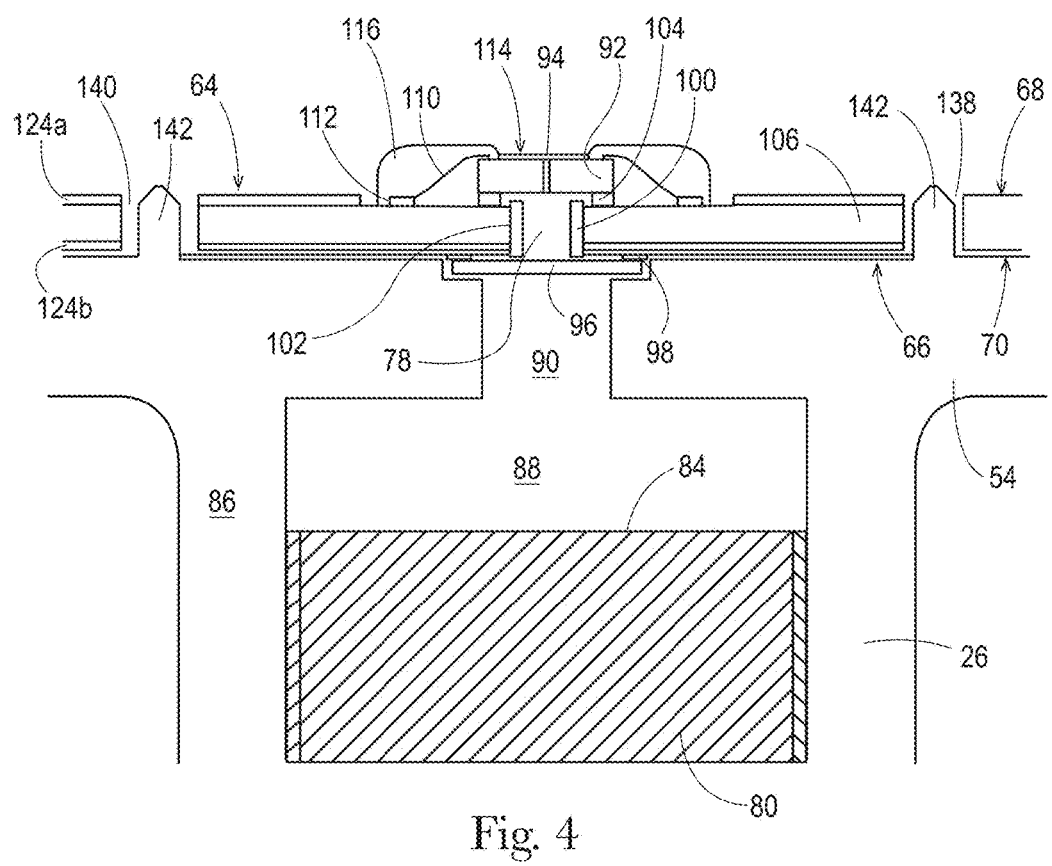

FIG. 4 is a cross-section schematic view of line 4-4 in FIG. 2B.

Figure 5A:
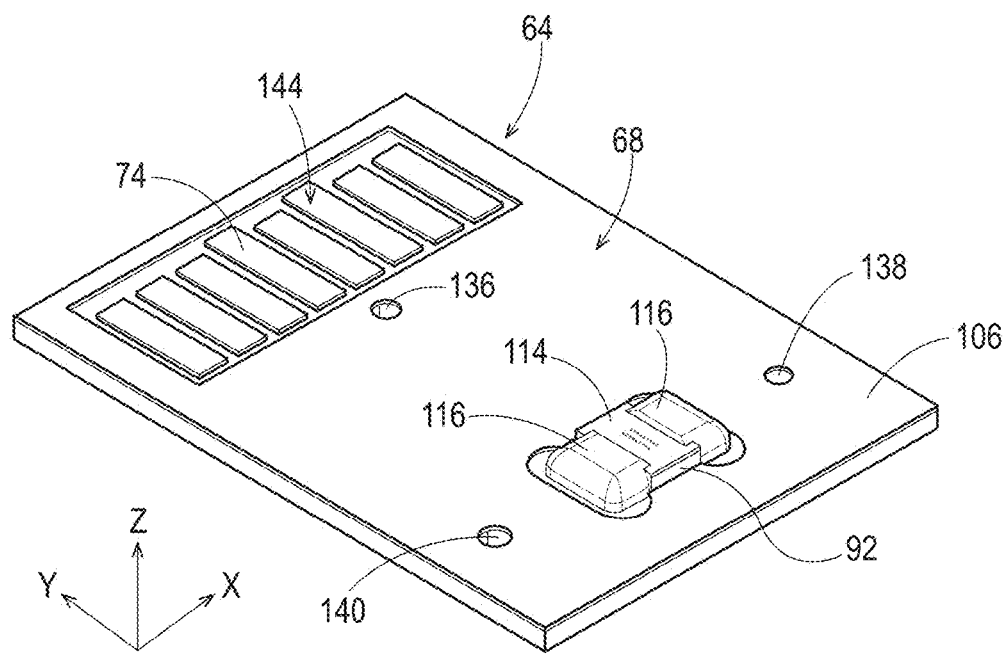
Figure 5B:
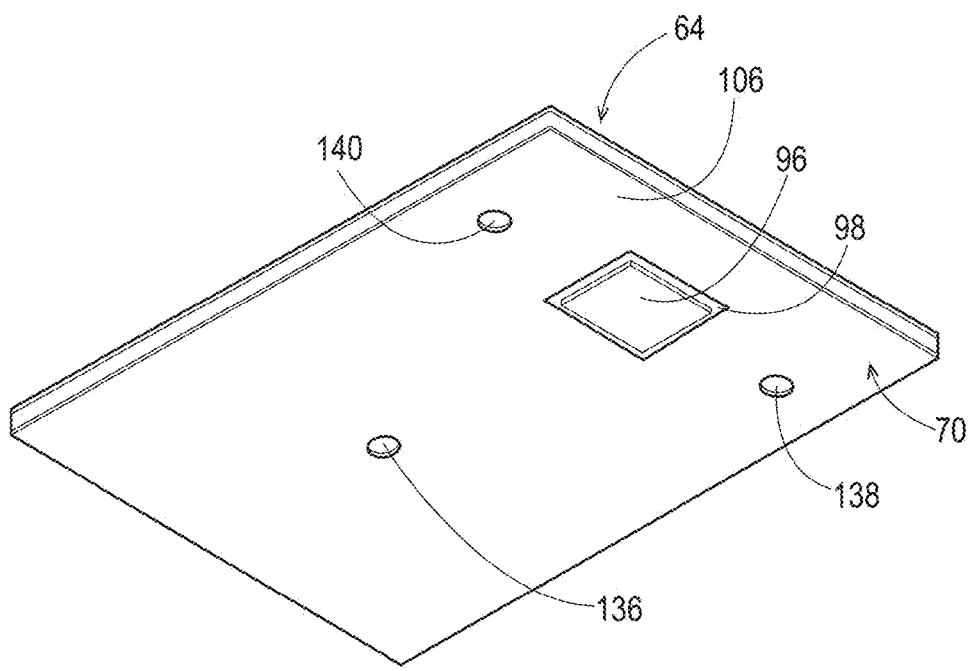

FIGS. 5A-5B are schematic isometric views of a microfluidic delivery member in accordance with an embodiment.

Figure 5C:
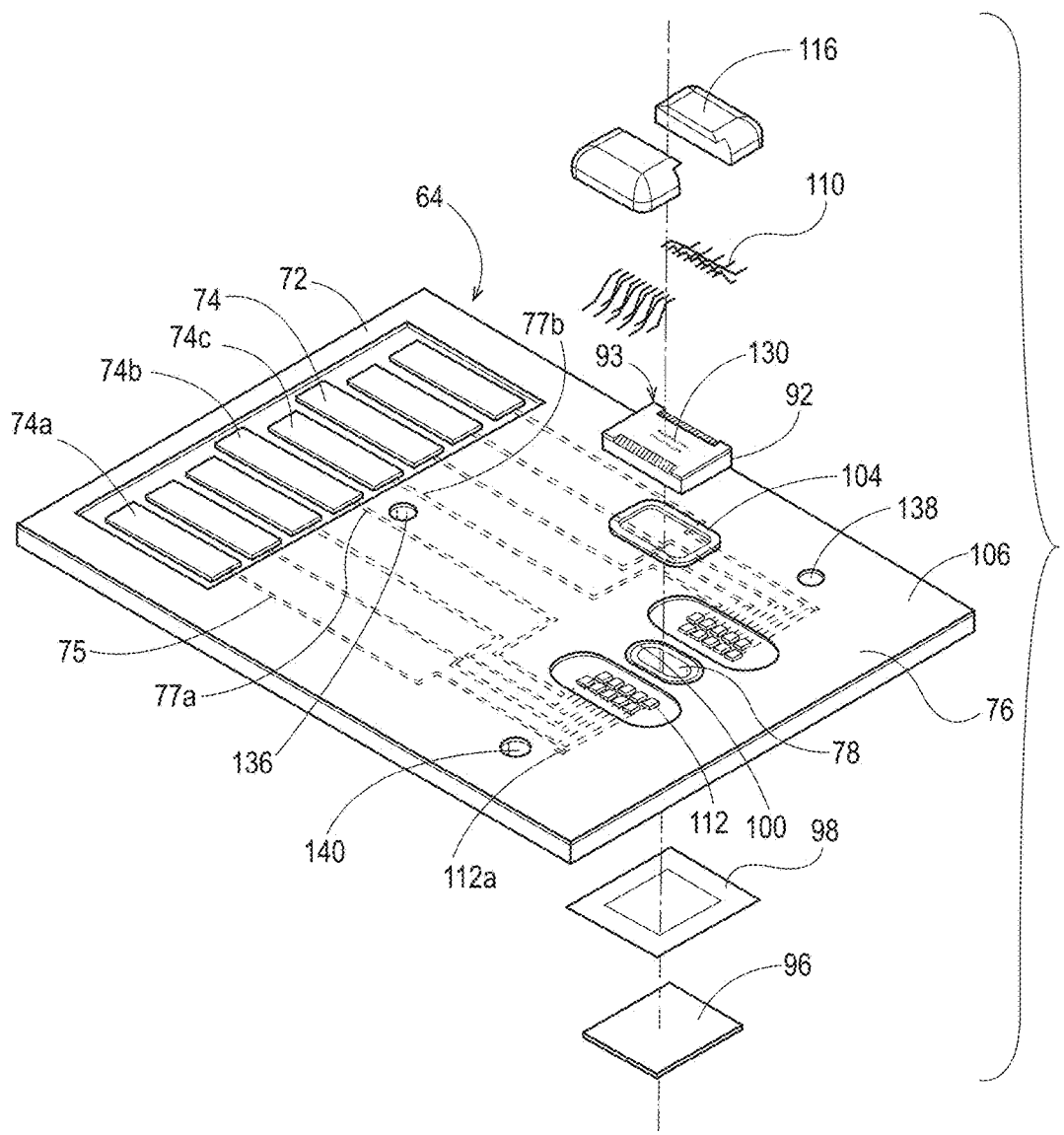

FIG. 5C is an exploded view of the structure in FIG. 5A.

Figure 6A:
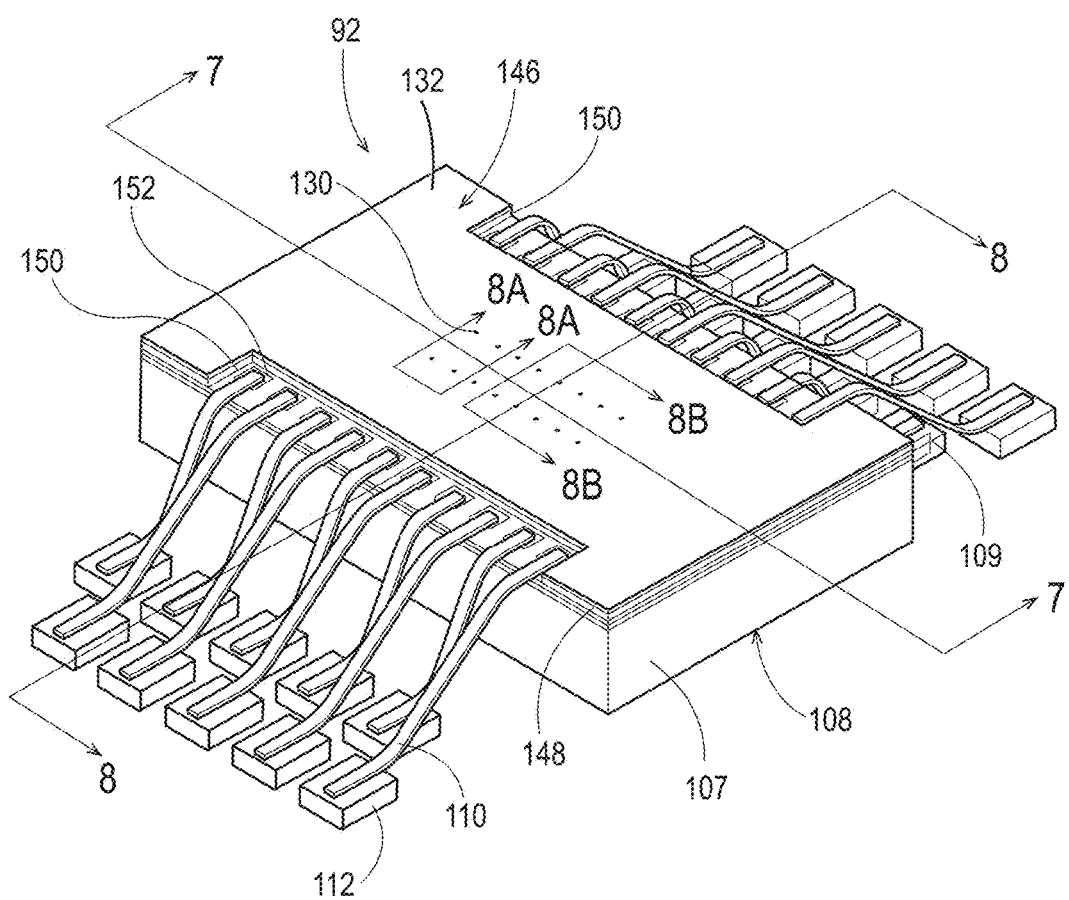
Figure 6B:
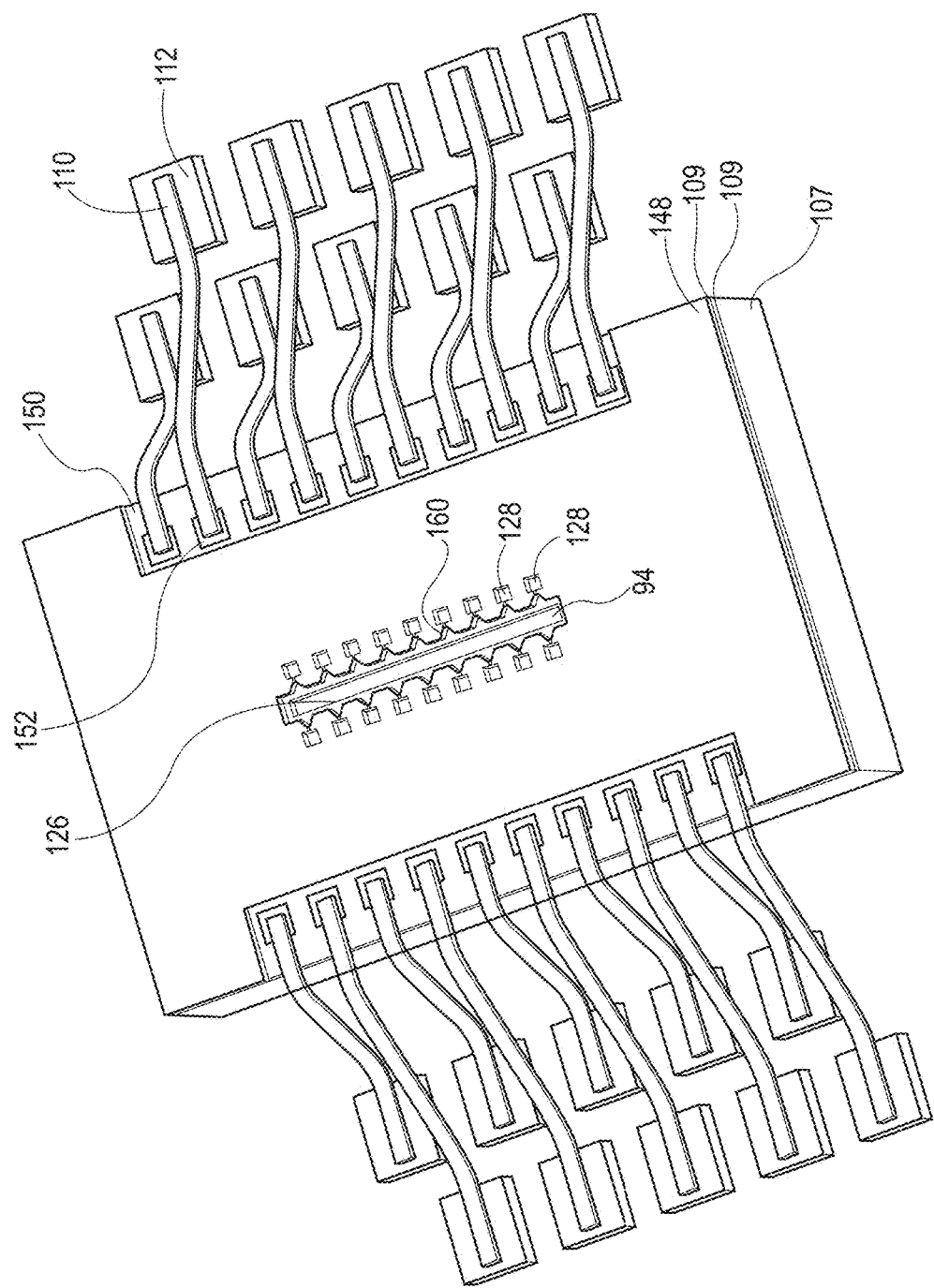
Figure 6C:
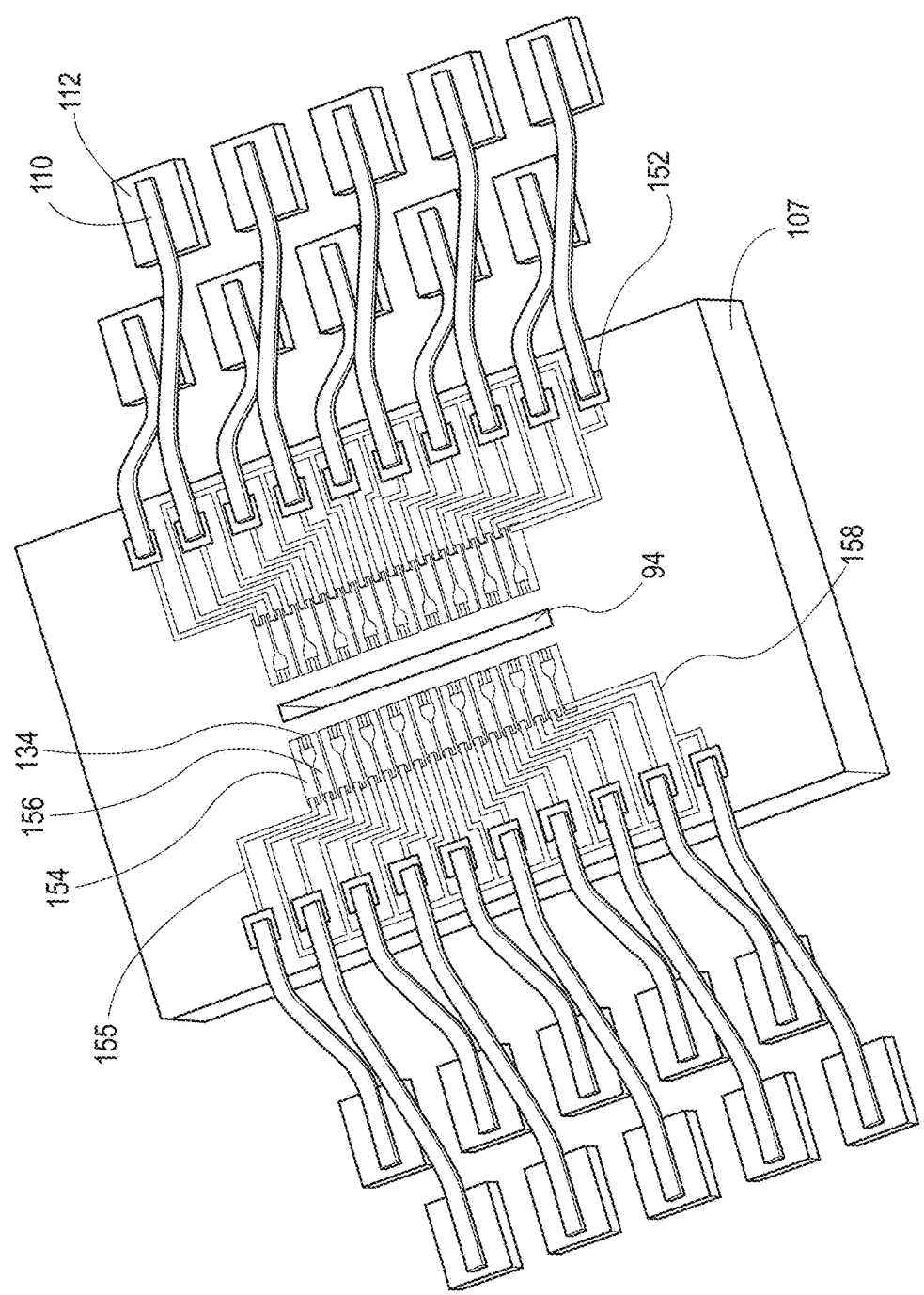

FIGS. 6A-6C are schematic isometric views of a microfluidic die at various layers in accordance with another embodiment.

Figure 7A:
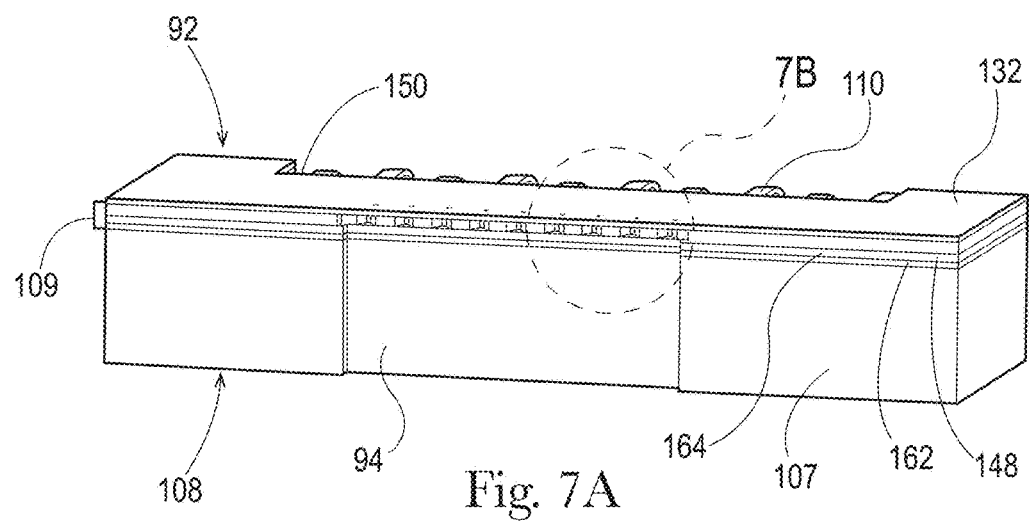

FIG. 7A is a cross-section schematic view of line 7-7 in FIG. 6.

Figure 7B:
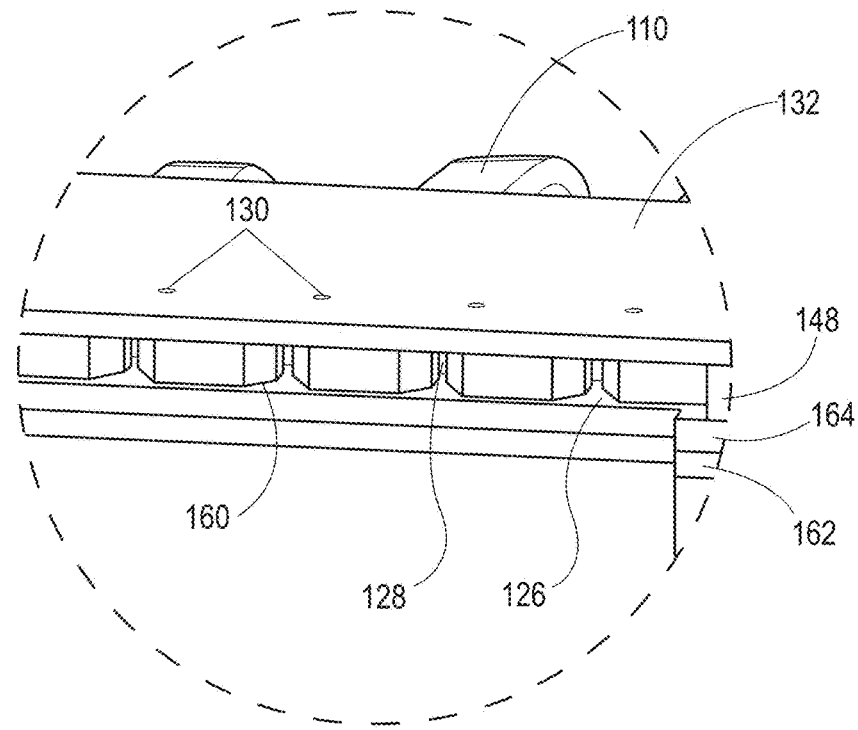

FIG. 7B is an enlarged view of a portion of FIG. 7A.

Figure 8A:
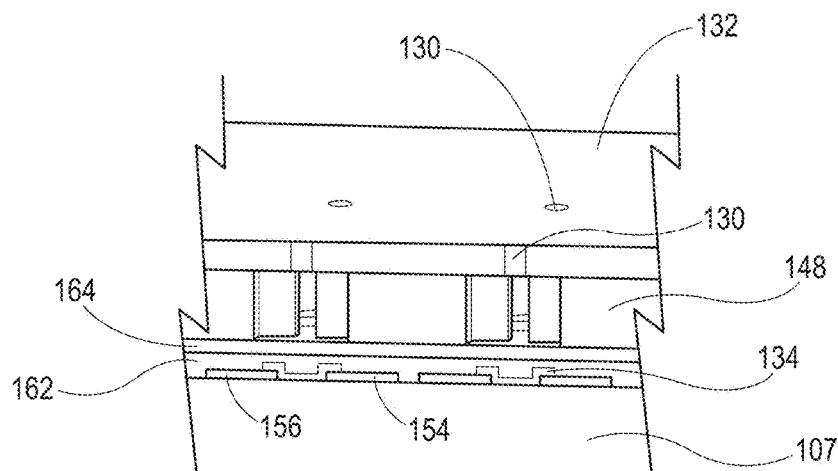

FIG. 8A is a cross-section view of line 8A-8A in FIG. 6A.

Figure 8B:
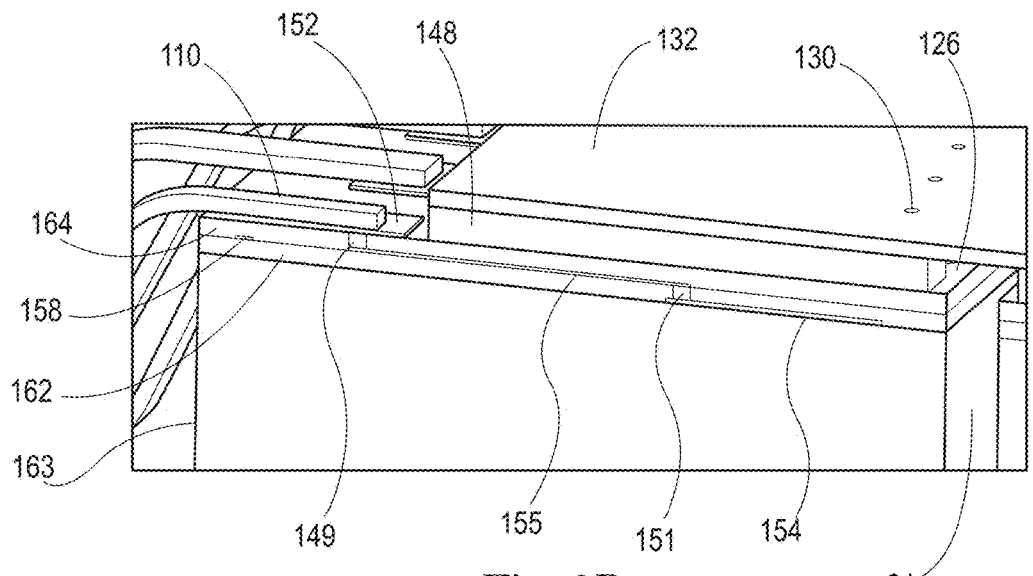

FIG. 8B is a cross-section view of line 8B-8B in FIG. 6A.

Figure 9:
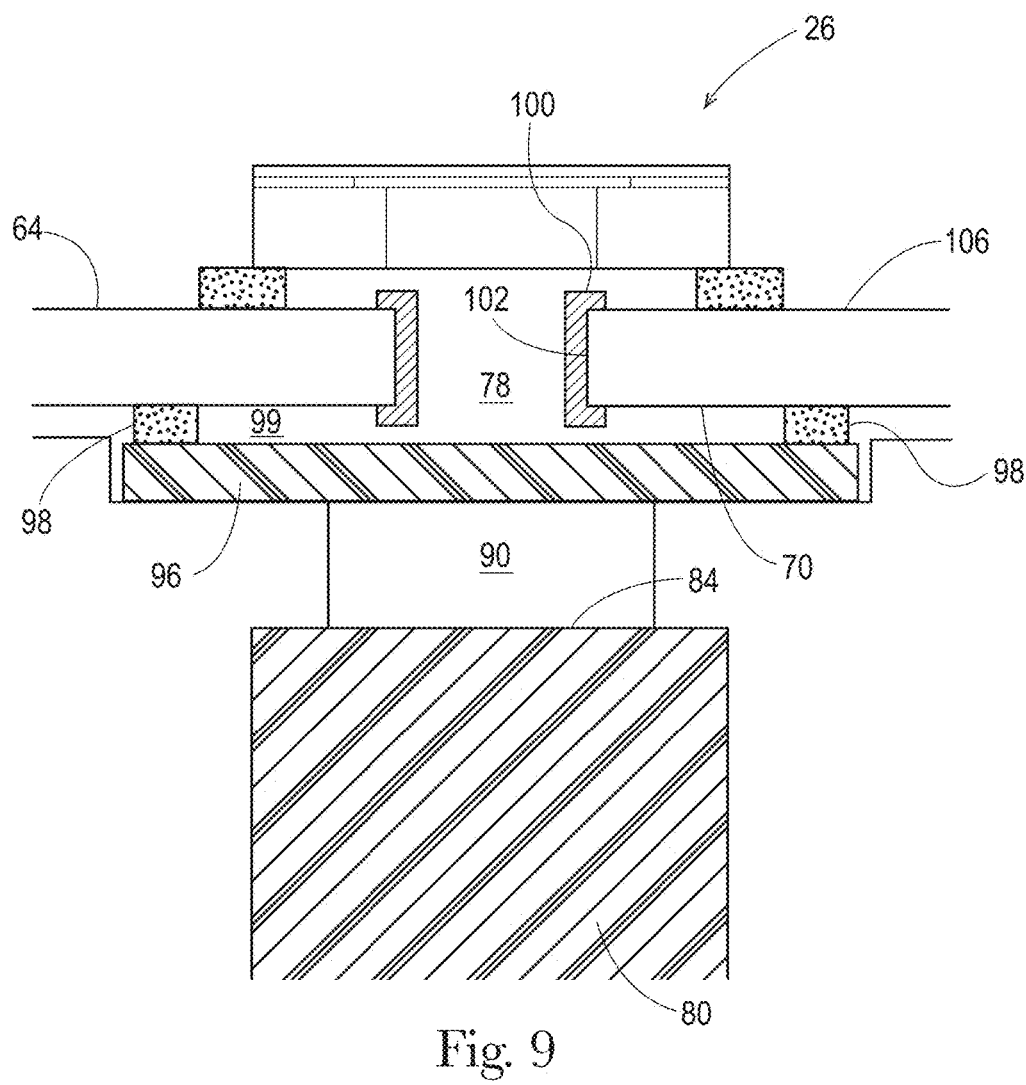

FIG. 9 is a cross-section schematic view of a fluid path of a microfluidic cartridge in accordance with one embodiment of the present invention.

Figure 10:
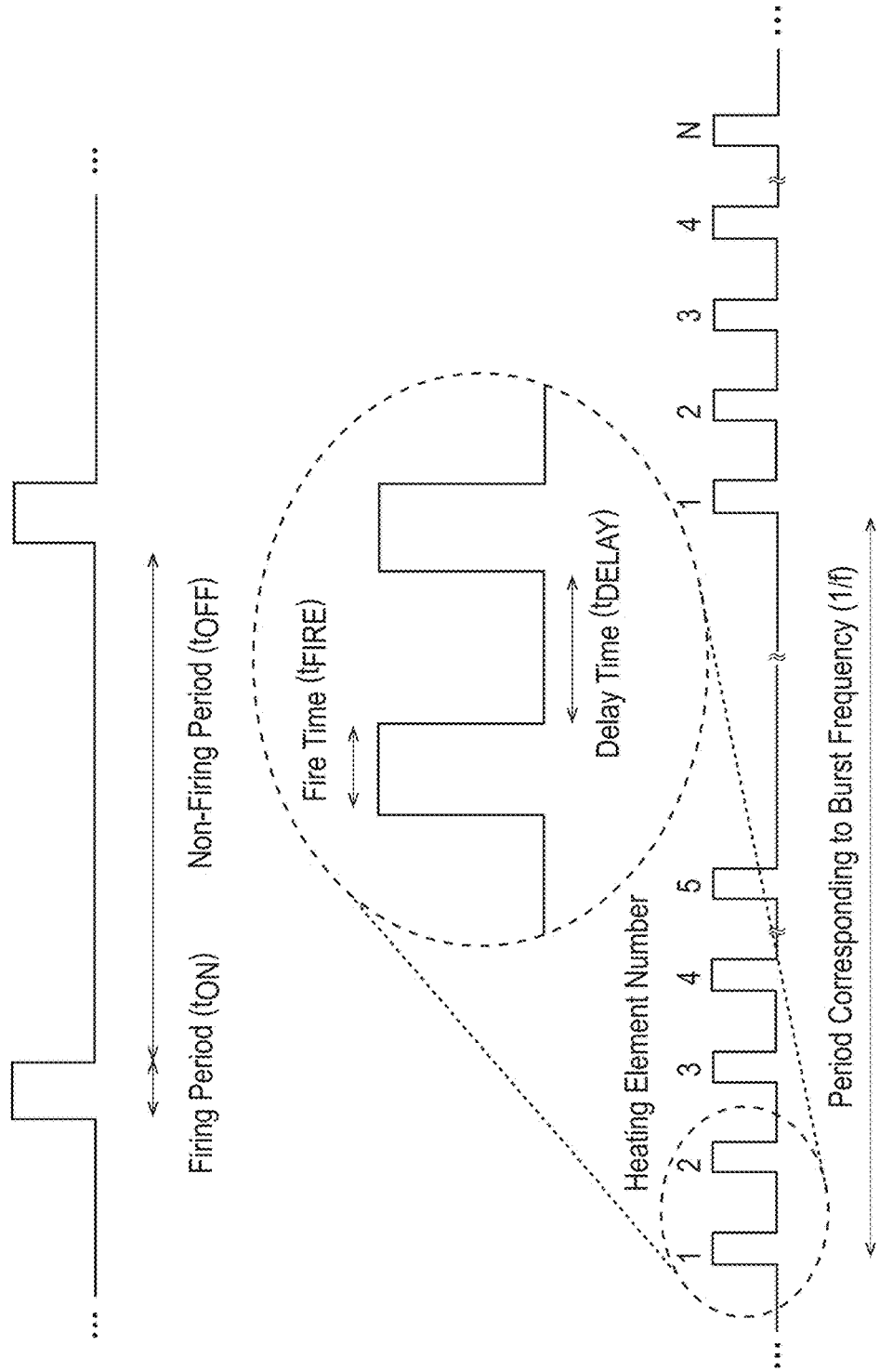

FIG. 10 is a diagram of wave forms and pulse timings of electrical signals in accordance with on embodiment of the present invention.

DETAILED DESCRIPTION OF EMBODIMENTS

The present invention provides a microfluidic delivery system 10 comprising a microfluidic delivery member 64 and methods for delivering fluid compositions into the air.

The delivery system 10 of the present invention may comprise a housing 12 and cartridge 26. The cartridge 26 may comprise a reservoir 50 for containing a volatile composition, and a microfluidic delivery member 64. The housing 12 may comprise a microprocessor and an outlet 20.

While the below description describes the delivery system 10 comprising a housing 12 and a cartridge 26, both having various components, it is to be understood that the delivery system 10 is not limited to the construction and arrangement set forth in the following description or illustrated in the drawings. The invention is applicable to other embodiments or may be practiced or carried out in various ways. For example, the components of the housing 12 may be located on the cartridge 26 and vice-versa. Further, the housing 12 and cartridge 26 may be configured as a single unit versus constructing a cartridge that is separable from the housing as described in the following description.

Housing

The microfluidic delivery system 10 may include a housing 12 constructed from a single piece or having multiple surfaces that are assembled to form the housing. The housing 12 may have an upper surface 14, a lower surface 16, and a body portion 18 between the upper and lower surfaces. The upper surface of the housing 12 includes an outlet 20 that places an environment external to the housing in fluid communication with an interior portion 22 of the housing 12. The interior portion 22 of the housing 12 may includes a holder member 24 that holds a microfluidic cartridge 26, which may be removable. As will be explained below, the microfluidic delivery system 10 may be configured to use thermal energy to deliver fluid from within the microfluidic fill cartridge 26 to an environment external to the housing 12.

Access to the interior portion 22 of the housing 12 is provided by an opening 28 in the housing. The opening 28 is accessible by a cover or door 30 of the housing 12. In the illustrated embodiment, the door 30 rotates to provide access to the opening 28.

The holder member 24 includes an upper surface 32 and a lower surface 34 that are coupled together by one or more sidewalls 36 and has an open side 38 through which the microfluidic cartridge 26 can slide in and out. The upper surface 32 of the holder member 24 includes an opening 40 that is aligned with the first hole 20 of the housing 12. The holder member 24 holds the microfluidic cartridge 26 in position.

The housing 12 may include external electrical connection elements for coupling with an external power source. The external electrical connection elements may be a plug configured to be plugged into an electrical outlet or battery terminals. Internal electrical connections couple the external electrical connection elements to the holder member 24 to provide power to the microfluidic cartridge 26. The housing 12 may include a power switch 42 on a front of the housing.

FIG. 2A shows the microfluidic cartridge 26 in the holder member 24 without the housing 12, and FIG. 2B shows the microfluidic cartridge 26 removed from the holder member 24. A circuit board 44 is coupled to the holder member by a screw 46. As will be explained in more detail below, the circuit board 44 includes electrical contacts 48 that electrically couple to the microfluidic cartridge 26. The electrical contacts 48 of the circuit board 44 are in electrical communication with the internal and external electrical connection elements.

Cartridge
Reservoir

The microfluidic delivery system 10 includes a microfluidic cartridge 26 which includes a reservoir 50 for containing a fluid composition. In some embodiments, the reservoir 50 is configured to contain from about 5 to about 50 ml, alternatively from about 10 to about 30 ml, alternatively from about 15 to about 20 ml of fluid composition. The delivery system may be configured to have multiple reservoirs, each containing the same or a different composition. The reservoir 50 may be formed as a separate construction, so as to be replaceable (e.g. a refill cartridge). The reservoir can be made of any suitable material for containing a fluid composition including glass and plastic.

A lid 54, having an inner surface 56 and an outer surface 58, is secured to an upper portion 60 of the reservoir to cover the reservoir 50. The lid 54 may be secured to the reservoir 50 via a variety of ways known in the art. Between the lid 54 and the reservoir 50, there may be an o-ring 62 for forming a seal therebetween to prevent fluid from leaking out of the reservoir.

A microfluidic delivery member 64 is secured to an upper surface 66 of the lid 54 of the microfluidic cartridge 26. The microfluidic delivery member 64 includes an upper surface 68 and a lower surface 70 (see FIGS. 5A-5C). A first end 72 of the upper surface 68 includes electrical contacts 74 for coupling with the electrical contacts 48 of the circuit board 44 when placed in the holder member 24. As will be explained in more detail below, a second end 76 of the microfluidic delivery member 64 includes a part of a fluid path that passes through an opening 78 for delivering fluid.

Fluid Transport Member

FIG. 3 is a cross-section view of the microfluidic cartridge 26 in the holder member 24 along line 3-3 shown in FIG. 2A. Inside the reservoir 50 is a fluid transport member 80 that has a first end 82 in the fluid 52 in the reservoir 50 and a second end 84 that is above the fluid. The second end 84 of the fluid transport member 80 is located below the microfluidic delivery member 64. The fluid transport member 80 delivers fluid from the reservoir 50 to the microfluidic delivery member 64. Fluid can travel by wicking, diffusion, suction, siphon, vacuum, or other mechanism. In some embodiments, the fluid may be transported to the microfluidic delivery member by a gravity fed system known in the art.

In some embodiments, the microfluidic delivery system 10 may include a fluid channel positioned in a flow path between the fluid transport member 80 and the reservoir 50 or between the fluid transport member 80 and the microfluidic delivery member 64. A channel may be useful in configurations where the reservoir, transport member or the microfluidic delivery member are not perfectly aligned vertically wherein the capillary fluid channel is used to still enable capillary flow of liquid.

The fluid transport member 80 may be any commercially available capillary tube or wicking material, such as a metal or fabric mesh, sponge, or fibrous or porous wick that contains multiple interconnected open cells which form capillary passages to draw a fluid composition up from the reservoir to come in contact with the fluid feed of the microfluidic delivery member. Non-limiting examples of suitable compositions for the fluid transport member include polyethylene, ultra-high molecular weight polyethelene, nylon 6, polypropylene, polyester fibers, ethyl vinyl acetate, polyether sulfone, polyvinylidene fluoride, and polyethersulfone, polytetrafluroethylene, and combinations thereof. In some embodiments, the fluid transport member 80 is free of a polyurethane foam. Many traditional ink jet cartridges use an open-cell polyurethane foam which can be incompatible with perfume mixtures over time (e.g. after 2 or 3 months) and can break down.

In some embodiments, the fluid transport member 80 may be a high density wick composition to aid in containing the scent of a perfume mixture. In one embodiment, the fluid transport member is made from a plastic material chosen from high-density polyethylene or polyester fiber. As used herein, high density wick compositions include any conventional wick material known in the art having a pore radius or equivalent pore radius (e.g. in the case of fiber based wicks) ranging from about 20 microns to about 200 microns, alternatively from about 30 microns to about 150 microns, alternatively from about 30 microns to about 125 microns, alternatively, about 40 microns to about 100 microns.

Regardless of the material of manufacture, where a wicking material is used, the fluid transport member 80 can exhibit an average pore size from about 10 microns to about 500 microns, alternatively from about 50 microns to about 150 microns, alternatively about 70 microns. The average pore volume of the wick, expressed as a fraction of the fluid transport member not occupied by the structural composition, is from about 15% to about 85%, alternatively from about 25% to about 50%. Good results have been obtained with wicks having an average pore volume of about 38%.

The fluid transport member 80 may be any shape that is able to deliver fluid from the reservoir 50 to the microfluidic delivery member 64. Although the fluid transport member 80 of the illustrated embodiment has a width dimension, such as diameter, that is significantly smaller than the reservoir 50, it is to be appreciated that the diameter of the fluid transport member 80 may be larger and in one embodiment substantially fills the reservoir 50. The fluid transport member 80 can also be of variable length, such as, from about 1 mm to about 100 mm, or from about 5 mm to about 75 mm, or from about 10 mm to about 50 mm.

As best shown in FIG. 4, the second end 84 of the fluid transport member 80 is surrounded by a transport cover 86 that extends from the inner surface of the lid 54. The second end 84 of the fluid transport member 80 and the transport cover 86 form a chamber 88. The chamber 88 may be substantially sealed between the transport cover 86 and the fluid transport member 80 to prevent air from the reservoir 50 from entering the chamber.

Microfluidic Delivery Member

The delivery system 10 of the present invention employs a microfluidic delivery member 64. Microfluidic delivery member 64 of the present invention may employ aspects of ink-jet print head systems.

In a typical "drop-on-demand" ink-jet printing process, a fluid is ejected through a very small orifice of a diameter typically about 0.0024 inches (5-50 microns) in the form of minute droplets by rapid pressure impulses. The rapid pressure impulses are typically generated in the print head by either expansion of a piezoelectric crystal vibrating at a high frequency or volatilization of a volatile composition (e.g. solvent, water, propellant) within the ink by rapid heating cycles. Thermal ink-jet printers employ a heating element within the print head to volatilize a portion of the composition that propels a second portion of fluid through the orifice nozzle to form droplets in proportion to the number of on/off cycles for the heating element. The fluid is forced out of the nozzle when needed. Conventional ink-jet printers are more particularly described in U.S. Pat. Nos. 3,465,350 and 3,465,351.

The microfluidic delivery member 64 of the present invention may employ aspects of any known ink-jet print head system or, more particularly, aspects of thermal ink-jet print heads. The microfluidic delivery member 64 of the present invention may be in electrical communication with a power source and may include a printed circuit board ("PCB") 106 and a microfluidic die 92 that is in fluid communication with the fluid transport member 80.

As shown in FIGS. 4 and 5A-5C, the microfluidic delivery member 64 may include a printed circuit board 106 ("PCB"). The board 106 is a rigid planar circuit board, having the upper and lower surfaces 68, 70. The microfluidic delivery member 64 may comprise a planar surface area of less than about 25 mm$^2$, or about 6 mm$^2$.

The board 106 includes first and second circular openings 136, 138 and an oval opening 140. Prongs 142 from the lid 54 extend through the openings 136, 138, 140 to ensure the board 106 is aligned with the fluid path appropriately. The oval opening 140 interacts with a wider prong so that the board 106 can only fit onto the lid 54 in one arrangement. Additionally, the oval openings allow for PCB and lid tolerances.

The board 106 is of a conventional construction. It may comprise a fiberglass-epoxy composite substrate material and layers of conductive metal, normally copper, on the top and bottom surfaces. The conductive layers are arranged into conductive paths through an etching process. The conductive paths are protected from mechanical damage and other environmental effects in most areas of the board by a photo-curable polymer layer, often referred to as a solder-mask layer. In selected areas, such as the liquid flow paths and wire bond attachment pads, the conductive copper paths are protected by an inert metal layer such as gold. Other material choices could be tin, silver, or other low reactivity, high conductivity metals.

Still referring to FIGS. 5A-5C, the board 106 may include all electrical connections—the contacts 74, the traces 75, and the contact pads 112—on the upper surface 68 of the board 106. For example, a top surface 144 of the electrical contacts 74 that couple to the housing are parallel to an x-y plane. The upper surface 68 of the board 106 is also parallel to the x-y plane. In addition, a top surface of the nozzle plate 132 of the die 92 is also parallel to the x-y plane. The contact pads 112 also have a top surface that is parallel to the x-y plane. By forming each of these features to be in parallel planes, the complexity of the board 106 may be reduced and is easier to manufacture. In addition, this allows nozzles 130 to eject the fluid vertically (directly up or at an angle) away from the housing 12, such as could be used for spraying scented oils into a room as air freshener. This arrangement could create a plume of fine droplets about 5 cm to about 10 cm upward away from the nozzles 130 and housing 12.

The board 106 includes the electrical contacts at the first end and contact pads 112 at the second end proximate the die 92. Electrical traces from the contact pads 112 to the electrical contacts are formed on the board and may be covered by the solder mask or another dielectric. Electrical connections from the die 92 to the board 106 may be established by a wire bonding process, where small wires, which may be composed of gold or aluminum, are thermally attached to bond pads on the silicon die and to corresponding bond pads on the board. An encapsulant material, normally an epoxy compound, is applied to the wire bond area to protect the delicate connections from mechanical damage and other environmental effects.

On the lower surface of the board 106, a filter 96 separates the opening 78 of the board from the chamber 88 at the lower surface of the board. The filter 96 is configured to prevent at least some of particulates from passing through the opening 78 to prevent clogging the nozzles 130 of the die 92. In some embodiments, the filter 96 is configured to block particulates that are greater than one third of the diameter of the nozzles 130. It is to be appreciated that, in some embodiments, the fluid transport member 80 can act as a suitable filter 96, so that a separate filter is not needed. In one embodiment, the filter 96 is a stainless steel mesh. In other embodiments, the filter 96 is randomly weaved mesh, polypropylene or silicon based.

The filter 96 may be attached to the bottom surface with an adhesive material that is not readily degraded by the fluid in the reservoir 50. In some embodiments, the adhesive may be thermally or ultraviolet activated. The filter 96 is positioned between the chamber 88 and the die 92. The filter 96 is separated from the bottom surface of the microfluidic delivery member 64 by a mechanical spacer 98. The mechanical spacer 98 creates a gap 99 between the bottom surface 70 of the microfluidic delivery member 64 and the filter 96 proximate the through hole 78. The mechanical spacer 98 may be a rigid support or an adhesive that conforms to a shape between the filter 96 and the microfluidic delivery member 64. In that regard, the outlet of the filter 96 is greater than the diameter of the second through hole 78 and is offset therefrom so that a greater surface area of the filter 96 can filter fluid than would be provided if the filter was attached directly to the bottom surface 70 of the microfluidic delivery member 64 without the mechanical spacer 98. It is to be appreciated that the mechanical spacer 98 allows suitable flow rates through the filter 96. That is, as the filter 96 accumulates particles, the filter will not slow down the fluid flowing therethrough. In one embodiment, the outlet of the filter 96 is about 4 mm$^2$ or larger and the standoff is about 700 microns thick.

The opening 78 may be formed as an oval, as is illustrated in FIG. 5C; however, other shapes are contemplated depending on the application. The oval may have the dimensions of a first diameter of about 1.5 mm and a second diameter of about 700 microns. The opening 78 exposes sidewalls 102 of the board 106. If the board 106 is an FR4 PCB, the bundles of fibers would be exposed by the opening. These sidewalls are susceptible to fluid and thus a liner 100 is included to cover and protect these sidewalls. If fluid enters the sidewalls, the board 106 could begin to deteriorate, cutting short the life span of this product.

The board 106 carries a microfluidic die 92. The die 92 comprises a fluid injection system made by using a semiconductor micro fabrication process such as thin-film deposition, passivation, etching, spinning, sputtering, masking, epitaxy growth, wafer/wafer bonding, micro thin-film lamination, curing, dicing, etc. These processes are known in the art to make MEMs devices. The die 92 may be made from silicon, glass, or a mixture thereof. The die 92 comprises a plurality of microfluidic chambers 128, each comprising a corresponding actuation element: heating element or electromechanical actuator. In this way, the die's fluid injection system may be micro thermal nucleation (e.g. heating element) or micro mechanical actuation (e.g. thin-film piezoelectric). One type of die for the microfluidic delivery member of the present invention is an integrated membrane of nozzles obtained via MEMs technology as described in U.S. 2010/0154790, assigned to STMicroelectronics; Geneva, Switzerland. In the case of a thin-film piezo, the piezoelectric material (e.g. lead zirconinum titanate)" is typically applied via spinning and/or sputtering processes. The semiconductor micro fabrication process allows one to simultaneously make one or thousands of MEMS devices in one batch process (a batch process comprises of multiple mask layers).

The die 92 is secured to the upper surface of the board 106 above the opening 78. The die 92 is secured to the upper surface of the board 106 by any adhesive material configured to hold the semiconductor die to the board. The adhesive material may be the same or different from the adhesive material used to secure the filter 96 to the microfluidic delivery member 64.

The die 92 may comprise a silicon substrate, conductive layers, and polymer layers. The silicon substrate forms the supporting structure for the other layers, and contains a channel for delivering fluid from the bottom of the die to the upper layers. The conductive layers are deposited on the silicon substrate, forming electrical traces with high conductivity and heaters with lower conductivity. The polymer layers form passages, firing chambers, and nozzles 130 which define the drop formation geometry.

FIGS. 6A-6C include more details of the microfluidic die 92. The microfluidic die 92 includes a substrate 107, a plurality of intermediate layers 109, and a nozzle plate 132. The plurality of intermediate layers 109 include dielectric layers and a chamber layer 148 that are positioned between the substrate and the nozzle plate 132. In one embodiment, the nozzle plate 132 is about 12 microns thick.

The die 92 includes a plurality of electrical connection leads 110 that extend from one of the intermediate layers 109 down to the contact pads 112 on the circuit board 106. At least one lead couples to a single contact pad 112. Openings 150 on the left and right side of the die 92 provide access to the intermediate layers 109 to which the leads 110 are coupled. The openings 150 pass through the nozzle plate 132 and chamber layer 148 to expose contact pads 152 that are formed on the intermediate dielectric layers. In other embodiments that will be described below, there may be one opening 150 positioned on only one side of the die 92 such that all of the leads that extend from the die extend from one side while other side remains unencumbered by the leads.

The nozzle plate 132 may include about 4 to about 64 nozzles 130, or about 6 to about 48 nozzles, or about 8 to about 32 nozzles, or about 8 to about 24 nozzles, or about 12 to about 20 nozzles. In the illustrated embodiment, there are eighteen nozzles 130 through the nozzle plate 132, nine nozzles on each side of a center line. Each nozzle 130 may deliver about 1 to about 10 picoliters, or about 2 to about 8 picoliters, or about 4 to about 6 picoliters of a fluid composition per electrical firing pulse. The nozzles 130 may be positioned about 60 um to about 110 μm apart. In one embodiment, twenty nozzles 130 are present in a 3 mm² area. The nozzles 130 may have a diameter of about 5 μm to about 40 μm, or 10 μm to about 30 μm, or about 20 μm to about 30 μm, or about 13 μm to about 25 μm. FIG. 6B is a top down isometric view of the die 92 with the nozzle plate 132 removed, such that the chamber layer 148 is exposed.

Generally, the nozzles 130 are positioned along a fluidic feed channel through the die 92 as shown in FIGS. 7A and 7B. The nozzles 130 may include tapered sidewalls such that an upper opening is smaller than a lower opening. In this embodiment, the heater is square, having sides with a length. In one example, the upper diameter is about 13 μm to about 18 μm and the lower diameter is about 15 μm to about 20 μm. At 13 μm for the upper diameter and 18 μm for the lower diameter, this would provide an upper area of 132.67 μm and a lower area of 176.63 μm. The ratio of the lower diameter to the upper diameter would be around 1.3 to 1. In addition, the area of the heater to an area of the upper opening would be high, such as greater than 5 to 1 or greater than 14 to 1.

Each nozzle 130 is in fluid communication with the fluid in the reservoir 50 by a fluid path. Referring to FIG. 4 and FIGS. 7A and 7B, the fluid path from the reservoir 50 includes the first end 82 of the fluid transport member 80, through the transport member to the second end 84 of the transport member, through the chamber 88, through the first through-hole 90, through the opening 78 of the board 106, through an inlet 94 of the die 92, then through a channel 126, and then through the chamber 128, and out of the nozzle 130 of the die.

Proximate each nozzle chamber 128 is a heating element 134 (see FIGS. 6C and 8A) that is electrically coupled to and activated by an electrical signal being provided by one of the contact pads 152 of the die 92. Referring to FIG. 6C, each heating element 134 is coupled to a first contact 154 and a second contact 156. The first contact 154 is coupled to a respective one of the contact pads 152 on the die by a conductive trace 155. The second contact 156 is coupled to a ground line 158 that is shared with each of the second contacts 156 on one side of the die. In one embodiment, there is only a single ground line that is shared by contacts on both sides of the die. Although FIG. 6C is illustrated as though all of the features are on a single layer, they may be formed on several stacked layers of dielectric and conductive material. Further, while the illustrated embodiment shows a heating element 134 as the activation element, the die 92 may comprise piezoelectric actuators in each chamber 128 to dispense the fluid composition from the die.

In use, when the fluid in each of the chambers 128 is heated by the heating element 134, the fluid vaporizes to create a bubble. The expansion that creates the bubble causes fluid to eject from the nozzle 130 and to form a plume of one or more droplets.

FIG. 7A is a cross-section view through the die of FIG. 6, through cut lines 7-7. FIG. 7B is an enhanced view of the cross-section in FIG. 7A. The substrate 107 includes an inlet path 94 coupled to a channel 126 that is in fluid communication with individual chambers 128, forming part of the fluid path. Above the chambers 128 is the nozzle plate 132 that includes the plurality of nozzles 130. Each nozzle 130 is above a respective one of the chambers 128. The die 92 may have any number of chambers and nozzles, including one chamber and nozzle. In the illustrated embodiment, the die includes eighteen chambers each associated with a respective nozzle. Alternatively, it can have ten nozzles and two chambers provided fluid for a group of five nozzles. It is not necessary to have a one-to-one correspondence between the chambers and nozzles.

As best seen in FIG. 7B, the chamber layer 148 defines angled funnel paths 160 that feed the fluid from the channel 126 into the chamber 128. The chamber layer 148 is positioned on top of the intermediate layers 109. The chamber layer defines the boundaries of the channels and the plurality of chambers 128 associated with each nozzle 130. In one embodiment, the chamber layer is formed separately in a mold and then attached to the substrate. In other embodiments, the chamber layer is formed by depositing, masking, and etching layers on top of the substrate.

The intermediate layers 109 include a first dielectric layer 162 and a second dielectric layer 164. The first and second dielectric layers are between the nozzle plate and the substrate. The first dielectric layer 162 covers the plurality of first and second contacts 154, 156 formed on the substrate and covers the heaters 134 associated with each chamber. The second dielectric layer 164 covers the conductive traces 155.

FIG. 8A is a cross-section view through the die 92 along the cut line 8A-8A in FIG. 6A. The first and second contacts 154, 156 are formed on the substrate 107. The heaters 134 are formed to overlap with the first and second contacts 154, 156 of a respective heater assembly. The contacts 154, 156 may be formed of a first metal layer or other conductive material. The heaters 134 may be formed of a second metal layer or other conductive material. The heaters 134 are thin-film resistors that laterally connect the first and second contacts 154, 156. In other embodiments, instead of being formed directly on a top surface of the contacts, the heaters 134 may be coupled to the contacts 154, 156 through vias or may be formed below the contacts.

In one embodiment, the heater 134 is a 20-nanometer thick tantalum aluminum layer. In another embodiment, the heater 134 may include chromium silicon films, each having different percentages of chromium and silicon and each being 10 nanometers thick. Other materials for the heaters 134 may include tantalum silicon nitride and tungsten silicon nitride. The heaters 134 may also include a 30-nanometer cap of silicon nitride. In an alternative embodiment, the heaters 134 may be formed by depositing multiple thin-film layers in succession. A stack of thin-film layers combine the elementary properties of the individual layers.

A ratio of an area of the heater 134 to an area of the nozzle 130 may be greater than seven to one. In one embodiment, the heater 134 is square, with each side having a length 147. The length may be 47 microns, 51 microns, or 71 microns. This would have an area of 2209, 2601, or 5041 microns square, respectively. If the nozzle diameter is 20 microns, an area at the second end would be 314 microns square, giving an approximate ratio of 7 to 1, 8 to 1, or 16 to 1, respectively.

FIG. 8B is a cross-section view through the die along the cut line 8B-8B in FIG. 6A. A length of the first contact 154 can be seen adjacent to the inlet 94. A via 151 couples the first contact 154 to trace 155 that is formed on the first dielectric layer 162. The second dielectric layer 164 is on the trace 155. A via 149 is formed through the second dielectric layer 164 and couples the trace 155 to the contact pad 152. A portion of the ground line 158 is visible toward an edge 163 of the die, between the via 149 and the edge 163.

As can be seen in this cross-section, the die 92 is relatively simple and does not include complex integrated circuitry. This die 92 will be controlled and driven by an external microcontroller or microprocessor. The external microcontroller or microprocessor may be provided in the housing. This allows the board 64 and the die 92 to be simplified and cost effective.

This die 92 is a thermal heating die that is free of complicated active circuitry. In this embodiment, there are two metal or conductive levels formed on the substrate. These conductive levels include the contact 154 and the trace 155. In some embodiments, all of these features can be formed on a single metal level. This allows the die to be simple to manufacture and minimizes the number of layers of dielectric between the heater and the chamber.

Referring now to FIG. 9, there is provided a close-up view of a portion of a microfluidic cartridge 26 illustrating a flow path with a filter 96 between the second end 84 of the fluid transport member 80 and the die 92 in accordance with one embodiment. The second through hole 78 of the microfluidic delivery member 80 may include a liner 100 that covers exposed sidewalls 102 of the board 106. The liner 100 may be any material configured to protect the board 106 from degradation due to the presence of the fluid, such as to prevent fibers of the board from separating. In that regard, the liner 100 may protect against particles from the board 106 entering into the fluid path and blocking the nozzles 130. For instance, the second through hole 78 may be lined with a material that is less reactive to the fluid in the reservoir than the material of the board 106. In that regard, the board 106 may be protected as the fluid passes therethrough. In one embodiment, the through hole is coated with a metal material, such as gold.

Upon depletion of the fluid in the reservoir 50, the microfluidic cartridge 26 may be removed from the housing 10 and replaced with another microfluidic cartridge 26.

Operating System

The microfluidic delivery system 10 includes programmable electronic drive circuitry to set a precise intensity level and delivery rate (in milligrams per hour) of a fluid composition to provide a consumer benefit, such as good room-fill in large living spaces with minimal deposition and minimal clogging (e.g. wick clogging). In operation, the microfluidic delivery system 10 may deliver a spray of micro droplets in which the majority of emitted droplets project at least about 4 cm to about 12 cm, or about 8 cm to about 12 cm upward from the nozzles 130 to provide noticeable delivery of the fluid composition to a space while minimizing deposition.

The delivery system 10 may allow a user to adjust the intensity and/or the timing of delivering the fluid composition for personal preference, efficacy, or for room size. For example, the delivery system 10 may provide ten intensity levels for a user to select and user selected options of delivering the fluid composition every 6, 12, or 24 hours.

The microfluidic delivery system 10 can be run in one of two modes: (1) normal operation and (2) refill limited. In normal operation mode, the system is running at a frequency that enables the chambers 128 to refill to a degree substantially equal to their static sill volume such that droplet ejection is consistent in volume and shape. In contrast, refill limited mode is an operating condition whereby the drive circuitry fires at a rate faster than the time required for the fluid to substantially refill the chamber 128. By operating in the refill limited mode, the system 10 can force the drops that are ejected to have a smaller size, higher velocity, and random shape distribution which can lead to less deposition on the housing 12, microfluidic delivery member 64 or surrounding surfaces. These drops are typically smaller than the nozzle diameter at higher burst frequency. With printing applications this random shape and size can be problematic for high print resolution but it can be an advantage in the case of atomizing a liquid into the air. Operating in refill limited mode allows smaller droplets to be ejected while avoiding complex micro fabrication processes to construct small nozzle diameters, which may be more prone to clogging. The small droplet distribution may have the advantage of evaporating faster compared to a droplet distribution produced under normal operating mode, possibly minimizing surface deposition and far reaching in space due to diffusion kinetics.

The drive circuitry is powered by about 4 to about 24 Volts, or about 4 to about 16 Volts from an external power source. The heating element 134 is electrically connected to a microprocessor, which may be part of the device or cartridge and comprises software programmed to control operation of the heating element 134 such as firing time, firing sequence, and frequency of the heating element. When the heating element 134 is activated under the direction of the software, the fluid composition emits from the nozzles 130.

Referring to FIG. 10, the microprocessor supplies firing pulses having a fire time (denoted $t_{FIRE}$) to a heating element 134. In some embodiments as shown in FIG. 10, a plurality of individual heating elements are fired sequentially (1, 2, 3, 4, etc), with an interposed delay time (denoted $t_{DELAY}$), in a sequence referred to as a burst. Bursts occur at a burst frequency (denoted $f_{BURST}$) of about 100 to about 8000 Hertz, or about 100 to about 6000 Hertz, or about 1000 to about 6000 Hertz, or about 1000 to about 5000 Hertz, or about 2000 to 5000 Hertz or about 1000 to about 2500 Hertz, during a firing period (denoted $t_{ON}$). In an embodiment where heating elements 134 are configured to be fired sequentially, the burst frequency ($f_{BURST}$) is equivalent to the firing frequency of an individual nozzle.

It has been found that the firing frequency will impact droplet size as well as how far upward the droplet is ejected which is important for avoiding deposition. With higher rates (e.g. 5000 Hertz), the droplets are fired at 5000 times/second which provides more momentum for the following droplets and hence causes the droplets to be ejected further which may help reduce deposition on surrounding surfaces. In addition, at 5000 Hertz the droplets are smaller for a given chamber size due to insufficient time to completely fill the chamber which has been defined above as refill limited mode.

The firing period ($t_{ON}$) may have a duration of about 0.25 seconds to about 10 seconds, or about 0.5 seconds to about 2 seconds, or about 0.25 seconds to about 1 second. A non-firing period (denoted $t_{OFF}$)—where no firing pulses are supplied to the heating element 134, may have a duration of about 9 seconds to about 200 seconds. When in a continuous repeat mode the $t_{ON}$ and $t_{OFF}$ are repeated continuously over an extended period of time to deliver a desired mg/hr rate of fluid. For example, with a burst frequency of 5000 Hertz and a firing period ($t_{ON}$) of 0.5 seconds, each nozzle is firing 2500 times during that sequence. If the $t_{OFF}$ is 10 seconds, then the sequence will be repeated every 10.5 seconds or about 6 times/minute and the total firings of each nozzle would be 2500 multiplied by about 6 times/min or about 15,000 firings/min. This delivery rate, per table 1, with 20 nozzles firing will deliver about 90 mg/hour of fluid composition into the air.

In another example of continuous repeat mode at 5000 Hz, to deliver 5 mg/hr of fluid composition, the heating element 134 may have firing periods ($t_{ON}$) and non-firing periods ($t_{OFF}$) comprising a 0.3% duty cycle (e.g. 0.5 second firing and 160 seconds non-firing). To deliver 57 mg/hr, the heating element may have firing and non-firing periods comprising a 2.4% duty cycle (e.g. 0.5 second firing and 20 seconds non-firing). In the case of an electromechanical actuator as the activation element, the stated heating element could be a piezo element. Table 1 and FIG. 10 show a firing pattern for the heating element 134 of the 1 to 2 microsecond pulse is repeated at the rates below to achieve intensity levels from level 1 to level 10 (or 5 to 90 mg/hr).

TABLE 1

| Intensity | mg/hour | $t_{FIRE}$ | $t_{DELAY}$ | $t_{ON}$ (s) | $t_{OFF}$ (s) | $f_{BURST}$ (Hz) |
|---|---|---|---|---|---|---|
| 1 | 5 | 2 us | 8 us | .5 sec | 160 sec | 5000 |
| 2 | 10 | 2 us | 8 us | .5 sec | 100 sec | 5000 |
| 3 | 15 | 2 us | 8 us | .5 sec | 70 sec | 5000 |
| 4 | 20 | 2 us | 8 us | .5 sec | 50 sec | 5000 |
| 5 | 25 | 2 us | 8 us | .5 sec | 40 sec | 5000 |
| 6 | 31 | 2 us | 8 us | .5 sec | 30 sec | 5000 |
| 7 | 43 | 2 us | 8 us | .5 sec | 25 sec | 5000 |
| 8 | 57 | 2 us | 8 us | .5 sec | 20 sec | 5000 |
| 9 | 72 | 2 us | 8 us | .5 sec | 15 sec | 5000 |
| 10 | 90 | 2 us | 8 us | .5 sec | 10 sec | 5000 |

In boost mode, the heating elements 134 may have a firing period ($t_{ON}$) of about 0.5 seconds and a non-firing period ($t_{OFF}$) of about 0.5 seconds and repeated 20 times over approximately 20 seconds to deliver approximately 5 mg of fluid composition into the air. This number of repeats for a one-time boost can be adjusted with software as desired.

The chamber 128 dimensions (e.g. inlet width, inlet thickness, surface tension of the inlet flow paths as well as the liquid properties (surface tension and viscosity)) can all impact what is the desired frequency for either normal operation mode or refill limited mode. With a recent example, the inventors have found that firing frequency of less than 2000 Hertz tends to result in normal operation mode where as when the electrical signal fires at frequencies of 4000 Hertz or higher, the system tends to be in a refill limited mode with significantly smaller droplets relative to the nozzle diameter and more fine fragments. While refill limited mode may be a problem for printing ink onto paper with certain resolution, it is may be an advantage for systems designed to volatilize a liquid into the air or depositing compositions onto a surface.

As part of the operation of the heating element 134, it is possible to supply one or more preheating pulses with a preheating duration (denoted $t_{HEAT}$) which is always less than $t_{FIRE}$ for the sole purpose of preheating the liquid in the chamber. The level and rate of preheating is controlled by the number and duration of pulses supplied. The preheating of fluid could be important to lowering the viscosity of the system and hence making for more realizable firing of fluids. With lower viscosity, exit velocities are also higher which improves throw distance of the droplets.

As part of the operating conditions, under device ideal state, one can introduce a "keep wet spitting" ("KWS") operation for the sole purpose of maintaining nozzle health over time. KWS is firing operation at very low frequency in order to balance the dry out phenomenon with wasted delivered fluid. In the case of perfumes, a KWS of 0.1 to 0.0001 Hertz is sufficient to keep the nozzles healthy. Dry out is meant to be fluid compositional changes over time that impact jetting performance (e.g. viscosity, low BP constitutes, etc)

In multiple reservoir delivery systems, a microprocessor and timer could be installed to emit the fluid composition from individual reservoirs at different times and for selected time periods, including emitting the volatile compositions in an alternating emission pattern as described in U.S. Pat. No. 7,223,361. Additionally, the delivery system could be programmable so a user can select certain compositions for emission. In the case of scented perfumes being emitted simultaneously, a customized scent may be delivered to the air. It is also understood that in a multi chamber system the drive circuitry (voltage, $t_{FIRE}$, $t_{HEAT}$, etc) could be different in the same device While the heating element 134 for each chamber 128 is illustrated in FIG. 10 sequentially, the heating elements could be activated simultaneously, or in a pre-determined pattern/sequence (e.g. row 1: nozzles 1, 5, 10, 14, 18; etc. . . . ). In some embodiments, the heating elements are pulsed in a staged manner since this may avoid coalescence of adjacent droplets but also avoids high power draws that may drain a battery faster. Ideally, the heating elements 134 are pulsed sequentially and preferably in a sequence that skips nozzles such that no two adjacent nozzles are ejecting fluid in sequence. In some embodiments, 20% of the heating elements 134 are fired simultaneously and then next 20% are fired, etc. In such an embodiment, it is preferred but not necessary that no two adjacent nozzles eject fluid simultaneously.

The nozzles 130 may be grouped together with other nozzles to form a group in which each group may be spaced from each other by at least a predetermined minimum number of nozzles. And, each of the nozzles 130 in a group is spaced from the nozzles in the subsequently enabled group by at least the predetermined minimum number of nozzles.

In some embodiments, the operating system of the microfluidic delivery system 10 delivers from about 5 mg to about 90 mg, or about 5 mg to about 40 mg, of fluid composition per hour into the air. Delivery rate of fluid composition can be calculated according to the following:

Average droplet mass*number of nozzles*frequency*cumulative seconds of $t_{ON}$/hour (sec/hr)=5 to 90 mg/hr.

For example, if $t_{ON}$ is 0.5 sec and $t_{OFF}$ is 59.5 seconds then cumulative $t_{ON}$ time would be 30 second/hour. Further, if average droplet mass is 0.000004 mg and one is using 20 nozzles at 5000 Hertz frequency the mg/hour with cumulative $t_{ON}$ of 30 seconds=12 mg/hour.

Optional Features

Fan

In another aspect of the invention, the delivery system may comprise a fan to assist in driving room-fill and to help avoid deposition of larger droplets from landing on surrounding surfaces that could damage the surface. The fan may be any known fan, such as a 5V 25×25×5 mm DC axial fan (Series 250, Type255N from EBMPAPST), used in the art for air freshening systems that delivers 1-1000 cubic centimeters of air/minute, alternatively 10-100 cubic centimeters/minute.

Sensors

In some embodiments, the delivery system may include commercially available sensors that respond to environmental stimuli such as light, noise, motion, and/or odor levels in the air. For example, the delivery system can be programmed to turn on when it senses light, and/or to turn off when it senses no light. In another example, the delivery system can turn on when the sensor senses a person moving into the vicinity of the sensor. Sensors may also be used to monitor the odor levels in the air. The odor sensor can be used to turn-on the delivery system, increase the heat or fan speed, and/or step-up the delivery of the fluid composition from the delivery system when it is needed.

In some embodiments, a VOC sensors can be used to measure intensity of perfume from adjacent or remote devices and alter the operational conditions to work synergistically with other perfume devices. For example a remote sensor could detect distance from the emitting device as well as fragrance intensity and then provide feedback to device on where to locate device to maximize room fill and/or provide the "desired" intensity in the room for the user.

In some embodiments, the devices can communicate with each other and coordinate operations in order to work synergistically with other perfume devices.

The sensor may also be used to measure fluid levels in the reservoir or count firing of the heating elements to indicate the cartridge's end-of-life in advance of depletion. In such case, an LED light may turn on to indicate the reservoir needs to be filled or replaced with a new reservoir.

The sensors may be integral with the delivery system housing or in a remote location (i.e. physically separated from the delivery system housing) such as remote computer or mobile smart device/phone. The sensors may communicate with the delivery system remotely via low energy blue tooth, 6 low pan radios or any other means of wirelessly communicating with a device and/or a controller (e.g. smart phone or computer).

In another embodiment, the user can change the operational condition of the device remotely via low energy blue tooth, or other means.

Smart Chip

In another aspect of this invention, the cartridge has a memory in order to transmit optimal operational condition to the device. We expect operational optimal condition for be fluid dependent in some cases.

The delivery system may be configured to be compact and easily portable. In such case, the delivery system may be battery operated. The delivery system may be capable for use with electrical sources as 9-volt batteries, conventional dry cells such as "A", "AA", "AAA", "C", and "D" cells, button cells, watch batteries, solar cells, as well as rechargeable batteries with recharging base.

Fluid Composition

To operate satisfactorily in a microfluidic delivery system, many characteristics of a fluid composition are taken into consideration. Some factors include formulating fluids with viscosities that are optimal to emit from the microfluidic delivery member, formulating fluids with limited amounts or no suspended solids that would clog the microfluidic delivery member, formulating fluids to be sufficiently stable to not dry and clog the microfluidic delivery member, etc. Operating satisfactorily in a microfluidic delivery system, however, addresses only some of the requirements necessary for a fluid composition having more than 50 wt. % of a perfume mixture to atomize properly from a microfluidic delivery member and to be delivered effectively as an air freshening or malodor reducing composition.

The fluid composition of the present invention may exhibit a viscosity of less than 20 centipoise ("cps"), alternatively less than 18 cps, alternatively less than 16 cps, alternatively from about 5 cps to about 16 cps, alternatively about 8 cps to about 15 cps. And, the volatile composition may have surface tensions below about 35, alternatively from about 20 to about 30 dynes per centimeter. Viscosity is in cps, as determined using the Bohlin CVO Rheometer system in conjunction with a high sensitivity double gap geometry.

In some embodiments, the fluid composition is free of suspended solids or solid particles existing in a mixture wherein particulate matter is dispersed within a liquid matrix. Free of suspended solids is distinguishable from dissolved solids that are characteristic of some perfume materials.

In some embodiments, the fluid composition of the present invention may comprise volatile materials. Exemplary volatile materials include perfume materials, volatile dyes, materials that function as insecticides, essential oils or materials that acts to condition, modify, or otherwise modify the environment (e.g. to assist with sleep, wake, respiratory health, and like conditions), deodorants or malodor control compositions (e.g. odor neutralizing materials such as reactive aldehydes (as disclosed in U.S. 2005/0124512), odor blocking materials, odor masking materials, or sensory modifying materials such as ionones (also disclosed in U.S. 2005/0124512)).

The volatile materials may be present in an amount greater than about 50%, alternatively greater than about 60%, alternatively greater than about 70%, alternatively greater than about 75%, alternatively greater than about 80%, alternatively from about 50% to about 100%, alternatively from about 60% to about 100%, alternatively from about 70% to about 100%, alternatively from about 80% to about 100%, alternatively from about 90% to about 100%, by weight of the fluid composition.

The fluid composition may contain one or more volatile materials selected by the material's boiling point ("B.P."). The B.P. referred to herein is measured under normal standard pressure of 760 mm Hg. The B.P. of many perfume ingredients, at standard 760 mm Hg can be found in "Perfume and Flavor Chemicals (Aroma Chemicals)," written and published by Steffen Arctander, 1969.

In the present invention, the fluid composition may have an average B.P. of less than 250° C., alternatively less than 225° C., alternatively less than 200° C., alternatively less than about 150° C., alternatively less than about 120° C., alternatively less than about 100° C., alternatively about 50° C. to about 200° C., alternatively about 110° C. to about 140° C. In some embodiments a quantity of low B.P. ingredients (<200 C) can be used to help higher B.P. formulations to be ejected. In one example, a formula with BP above 25° could be made to eject with good performance if 10-50% of the formula's ingredients has a B.P. less than 200 C despite the overall average still being above 250° C.

In some embodiments, the fluid composition may comprise, consist essentially of, or consist of volatile perfume materials.

Tables 2 and 3 outline technical data on perfume materials suitable for the present invention. In one embodiment, approximately 10%, by weight of the composition, is ethanol which may be used as a diluents to reduce boiling point to a level less than 250° C. Flash point may be considered in choosing the perfume formulation as flash points less than 70° C. require special shipping and handling in some countries due to flammability. Hence, there may be advantages to formulate to higher flash points.

Table 2 lists some non-limiting, exemplary individual perfume materials suitable for the fluid composition of the present invention.

TABLE 2

| CAS Number | Perfume Raw Material Name | B.P. (° C.) |
|---|---|---|
| 105-37-3 | Ethyl propionate | 99 |
| 110-19-0 | Isobutyl acetate | 116 |
| 928-96-1 | Beta gamma hexenol | 157 |
| 80-56-8 | Alpha Pinene | 157 |
| 127-91-3 | Beta Pinene | 166 |
| 1708-82-3 | cis-hexenyl acetate | 169 |
| 124-13-0 | Octanal | 170 |
| 470-82-6 | Eucalyptol | 175 |
| 141-78-6 | Ethyl acetate | 77 |

Table 3 shows an exemplary perfume mixture having a total B.P. less than 200° C.

TABLE 3

| CAS Number | Perfume Raw Material Name | Wt % | B.P. (° C.) |
|---|---|---|---|
| 123-68-2 | Allyl Caproate | 2.50 | 185 |
| 140-11-4 | Benzyl Acetate | 3.00 | 214 |
| 928-96-1 | Beta Gamma Hexenol | 9.00 | 157 |
| 18479-58-8 | Dihydro Myrcenol | 5.00 | 198 |
| 39255-32-8 | Ethyl 2 Methyl Pentanoate | 9.00 | 157 |
| 77-83-8 | Ethyl Methyl Phenyl Glycidate | 2.00 | 260 |
| 7452-79-1 | Ethyl-2-Methyl Butyrate | 8.00 | 132 |
| 142-92-7 | Hexyl Acetate | 12.50 | 146 |
| 68514-75-0 | Orange Phase Oil 25X1.18%-Low Cit. 14638 | 10.00 | 177 |
| 93-58-3 | Methyl Benzoate | 0.50 | 200 |
| 104-93-8 | Para Cresyl Methyl Ether | 0.20 | 176 |
| 1191-16-8 | Prenyl Acetate | 8.00 | 145 |
| 88-41-5 | Verdox | 3.00 | 223 |
| 58430-94-7 | Iso Nonyl Acetate | 27.30 | 225 |
| | TOTAL: | 100.00 | |

When formulating fluid compositions for the present invention, one may also include solvents, diluents, extenders, fixatives, thickeners, or the like. Non-limiting examples of these materials are ethyl alcohol, carbitol, diethylene glycol, dipropylene glycol, diethyl phthalate, triethyl citrate, isopropyl myristate, ethyl cellulose, and benzyl benzoate.

In some embodiments, the fluid composition may contain functional perfume components ("FPCs"). FPCs are a class of perfume raw materials with evaporation properties that are similar to traditional organic solvents or volatile organic compounds ("VOCs"). "VOCs", as used herein, means volatile organic compounds that have a vapor pressure of greater than 0.2 mm Hg measured at 20° C. and aid in perfume evaporation. Exemplary VOCs include the following organic solvents: dipropylene glycol methyl ether ("DPM"), 3-methoxy-3-methyl-1-butanol ("MMB"), volatile silicone oil, and dipropylene glycol esters of methyl, ethyl, propyl, butyl, ethylene glycol methyl ether, ethylene glycol ethyl ether, diethylene glycol methyl ether, diethylene glycol ethyl ether, or any VOC under the tradename of Dowanol™ glycol ether. VOCs are commonly used at levels greater than 20% in a fluid composition to aid in perfume evaporation.

The FPCs of the present invention aid in the evaporation of perfume materials and may provide a hedonic, fragrance benefit. FPCs may be used in relatively large concentrations without negatively impacting perfume character of the overall composition. As such, in some embodiments, the fluid composition of the present invention may be substantially free of VOCs, meaning it has no more than 18%, alternatively no more than 6%, alternatively no more than 5%, alternatively no more than 1%, alternatively no more than 0.5%, by weight of the composition, of VOCs. The volatile composition, in some embodiments, may be free of VOCs.

Perfume materials that are suitable as FPCs are disclosed in U.S. Pat. No. 8,338,346.

Throughout this specification, components referred to in the singular are to be understood as referring to both a single or plural of such component.

All percentages stated herein are by weight unless otherwise specified.

Every numerical range given throughout this specification will include every narrower numerical range that falls within such broader numerical range, as if such narrower numerical range were all expressly written herein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 6.1, 3.5 to 7.8, 5.5 to 10, etc.

Further, the dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A method of delivering a dose of a liquid composition from a microfluidic delivery refill, wherein the liquid composition comprises volatile components such that the liquid composition is defined by a boiling point temperature, and wherein the liquid composition comprises more than 50 wt. % of a perfume mixture, and wherein the microfluidic delivery refill comprises a reservoir enclosing the liquid composition and a microfluidic delivery member comprising a plurality of nozzles and a heater associated with each nozzle, wherein the microfluidic delivery member is in fluid communication with the reservoir, the method comprising:
receiving an electrical signal with one or more of the heaters of the microfluidic delivery member, wherein the electrical signal comprises a plurality of firing pulses that each alternate between a relatively low amplitude and a relatively high amplitude;
preheating the liquid composition before the heater of the microfluidic delivery member is activated, wherein the liquid composition is preheated for less than about 2 microseconds;
activating one or more non-adjacent heaters simultaneously in response to the relatively high amplitude of each of the firing pulses of the electrical signal, wherein, when the heater is activated, the temperature of the heater is greater than the boiling point temperature of the liquid composition, wherein only non-adjacent heaters are simultaneously activated, wherein the relatively high amplitude persists for a fire time (tFIRE) in each of the firing pulses, wherein the tFIRE is less than about 4 microseconds;
activating one or more of the heaters of the microfluidic delivery member in sequence in response to the relatively high amplitude of each of the firing pulses of the electrical signal, wherein no two adjacent nozzles are ejecting fluid in sequence;
utilizing an amount of energy while each heater is activated, wherein the amount of energy is between about 33 Milliwatts and about 8.5 Watts; and
vaporizing at least a portion of the volatile components of the liquid composition when each heater is activated, whereby the dose of the liquid composition is delivered by the microfluidic delivery member.

2. The method of claim 1, wherein:
the electrical signal comprises a firing period (tON) and a non-firing period (tOFF);
the plurality of firing pulses are pulsed during the firing period (tON) with an interposed delay time (tDELAY);
the electrical signal is maintained at the relatively low amplitude during the non-firing period (tOFF) and the interposed delay time (tDELAY); and
the plurality of firing pulses are pulsed at a burst frequency between about 1000 Hertz and about 8000 Hertz.

3. The method of claim 2, wherein:
the firing period (tON) comprises a burst of the firing pulses; and
the burst consists of between about 250 and about 80,000 of the firing pulses.

4. The method of claim 1, wherein the relatively high amplitude is between about 4 volts and about 16 volts.

5. The method of claim 1, wherein the heater has a resistance less than about 100 ohms.

6. The method of claim 1, wherein the dose delivered by the microfluidic delivery member is less than about 50 picoliters.

7. The method of claim 1, further comprising:
delivering additional doses of the liquid composition with the microfluidic delivery member, wherein the liquid composition is delivered at a rate between about 2 milligrams/hour and about 180 milligrams/hour.

8. The method of claim 1, wherein the boiling point temperature of the liquid composition is less than about 250° Celsius.

* * * * *